(12) United States Patent
Hanyu et al.

(10) Patent No.: US 11,819,846 B2
(45) Date of Patent: *Nov. 21, 2023

(54) SYSTEM FOR AGING INDUCTION, CONTROL DEVICE FOR AGING INDUCTION, METHOD FOR CONTROLLING AGING INDUCTION, AND PROGRAM FOR CONTROLLING AGING INDUCTION

(71) Applicant: Integriculture Inc., Tokyo (JP)

(72) Inventors: Yuki Hanyu, Tokyo (JP); Ikko Kawashima, Tokyo (JP)

(73) Assignee: Integriculture Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/952,513

(22) Filed: Sep. 26, 2022

(65) Prior Publication Data

US 2023/0124260 A1    Apr. 20, 2023

Related U.S. Application Data

(63) Continuation of application No. 16/098,232, filed as application No. PCT/JP2016/067599 on Jun. 13, 2016, now Pat. No. 11,484,879.

(30) Foreign Application Priority Data

May 2, 2016   (JP) ................................ 2016-092836

(51) Int. Cl.
*B01L 3/00*       (2006.01)
*G01N 33/483*    (2006.01)
(Continued)

(52) U.S. Cl.
CPC ..... *B01L 3/502715* (2013.01); *B01L 3/50273* (2013.01); *C12M 1/00* (2013.01);
(Continued)

(58) Field of Classification Search
CPC .......... B01L 2300/087; B01L 2400/04; B01L 3/502715; B01L 3/50273; C12M 1/00;
(Continued)

(56) References Cited

U.S. PATENT DOCUMENTS 5,399,493 A   3/1995  Emerson et al.
5,670,351 A   9/1997  Emerson et al.
(Continued)

FOREIGN PATENT DOCUMENTS

JP   2001-120261 A    5/2001
JP   2004-298087 A   10/2004
(Continued)

OTHER PUBLICATIONS

English translation of the International Preliminary Report on Patentability for International Application No. PCT/JP2016/067599, dated Nov. 6, 2018 (8 pages).
(Continued)

*Primary Examiner* — Lydia Edwards
(74) *Attorney, Agent, or Firm* — Clark & Elbing LLP

(57) ABSTRACT

In order to induce aging while cutting the costs associated with adding cytokines at different aging stages, in a system for aging induction including a first culture chamber for perfusing, with a culture medium, a subject of aging-induction, the subject of aging-induction being derived from a living organism; a second culture chamber for perfusing, with a culture medium, a secretor that secretes a cytokine; and a control device for aging induction including a detection unit, a memory unit and a control unit, a protocol for aging induction defining a procedure of aging induction is stored, and in the control unit, an aging state of the subject of aging-induction is detected with a detection unit, and based on the protocol for aging induction, a flow rate at which the culture medium containing the cytokine secreted (Continued)

by the secretor is supplied to the subject of aging-induction is controlled according to the aging state of the subject of aging-induction.

8 Claims, 22 Drawing Sheets

(51) Int. Cl.
*C12N 5/00* (2006.01)
*B01L 99/00* (2010.01)
*C12M 3/00* (2006.01)
*C12M 1/00* (2006.01)
*G16B 50/00* (2019.01)

(52) U.S. Cl.
CPC ............ *C12M 3/00* (2013.01); *C12N 5/0018* (2013.01); *G16B 50/00* (2019.02); *B01L 2300/087* (2013.01); *B01L 2400/04* (2013.01); *C12N 2501/20* (2013.01)

(58) Field of Classification Search
CPC .... C12M 3/00; C12N 2501/20; C12N 5/0018; G16B 50/00
See application file for complete search history.

(56) References Cited

U.S. PATENT DOCUMENTS

| | | | |
|---|---|---|---|
| 8,361,412 B2 | 1/2013 | Yasuda et al. |
| 8,771,931 B2 | 7/2014 | Tsuji et al. |
| 2006/0110822 A1 | 5/2006 | Robbins et al. |
| 2007/0104679 A1 | 5/2007 | Obinata et al. |
| 2011/0319868 A1 | 12/2011 | Hiles et al. |
| 2012/0149110 A1 | 6/2012 | Kitamura et al. |
| 2013/0177972 A1 | 7/2013 | Green et al. |
| 2015/0359940 A1 | 12/2015 | Hiles et al. |
| 2016/0082157 A1 | 3/2016 | Hiles et al. |

FOREIGN PATENT DOCUMENTS

| | | | |
|---|---|---|---|
| JP | 2008-513013 A | 5/2008 |
| JP | 4601423 B2 | 12/2010 |
| JP | 2013-510590 A | 3/2013 |
| JP | 2013-528072 A | 7/2013 |
| JP | 2014-018180 A | 2/2014 |
| JP | 5797113 B2 | 10/2015 |
| JP | 5881422 B2 | 3/2016 |
| KR | 10-2015-0042316 A | 4/2015 |
| WO | WO-2006/033935 A2 | 3/2006 |

OTHER PUBLICATIONS

English translation of the Written Opinion of the International Searching Authority for International Application No. PCT/JP2016/067599, dated Sep. 20, 2016 (7 pages).

International Search Report for International Application No. PCT/JP2016/067599, dated Sep. 20, 2016 (5 pages) (English language translation provided).

Kato et al., "Changes in the emulsifying and foaming properties of proteins during heat denaturation," Agric Biol Chem. 47(1):33-37 (1983).

Written Opinion of the International Searching Authority for International Application No. PCT/JP2016/067599, dated Sep. 20, 2016 (5 pages) (English language translation not provided).

FIG. 8A

| CONDITIONS | SUBJECT | MANUAL OF CULTURE | |
|---|---|---|---|
| | | THRESHOLD | OPERATION |
| INITIAL STATE | NONE | NONE | OPEN FLOW PATH FROM SECRETORY CELLS 50 TO SECRETORY CELLS 51 |
| PERFORMED AT OR ABOVE THRESHOLD | CONC. A | 0.1ng/L | CLOSE FLOW PATH FROM SECRETORY CELLS 50 TO SECRETORY CELLS 51 |
| PERFORMED AT OR ABOVE THRESHOLD | CONC. B | 0.1ng/L | CLOSE FROM SECRETORY CELLS 51 TO INTERNAL ORGAN 41 AND OPEN FROM SECRETORY CELLS 50 TO INTERNAL ORGAN |
| PERFORMED AT OR ABOVE THRESHOLD | CONC. C | 0.2ng/L | SEND A MESSAGE OF COMPLETION OF CULTURING INTERNAL ORGAN 41 |

FIG. 8B

| KIND OF CELLS | POSITION INFORMATION OF HORMONE-SECRETING CELLS |
|---|---|
| | PLACE CONTAINED |
| SECRETORY CELLS 50 | CONTAINER 60 |
| SECRETORY CELLS 51 | CONTAINER 61 |
| SECRETORY CELLS 52 | CONTAINER 62 |

FIG. 11A

| CONDITIONS | SUBJECT | THRESHOLD | MANUAL OF CULTURE | |
|---|---|---|---|---|
| | | | OPERATION | |
| INITIAL STATE | NONE | NONE | OPEN FLOW PATH FROM PLACENTAL CELLS TO SECRETORY CELLS | |
| PERFORMED AT OR ABOVE THRESHOLD | GROWTH FACTORS | 50 μg/L | CLOSE FLOW PATH FROM PLACENTAL CELLS TO SECRETORY CELLS | |
| PERFORMED AT OR ABOVE THRESHOLD | SERUM COMPONENTS | 45 μg/L | CLOSE FROM HEPATIC CELLS TO MYOBLASTS AND OPEN FROM PLACENTAL CELLS TO MYOBLASTS | |
| PERFORMED AT OR ABOVE THRESHOLD | SIGNALING MOLECULES | 30 μg/L | SEND A MESSAGE OF COMPLETION OF CULTURING MYOBLASTS | |

FIG. 11B

| KIND OF CELLS | POSITION INFORMATION OF HORMONE SECRETING CELLS |
|---|---|
| | PLACE CONTAINED |
| PLACENTAL CELLS | CONTAINER 60 |
| HEPATIC CELLS | CONTAINER 61 |
| MYOBLASTS | VESSEL 40 |

** P ≤ 0.01 COMPARED WITH Ct

SYSTEM FOR AGING INDUCTION, CONTROL DEVICE FOR AGING INDUCTION, METHOD FOR CONTROLLING AGING INDUCTION, AND PROGRAM FOR CONTROLLING AGING INDUCTION

TECHNICAL FIELD

The present invention relates to systems for aging induction, control devices for aging induction, methods for controlling aging induction, and programs for controlling aging induction.

BACKGROUND ART

A variety of culture devices and methods have been developed for the purpose of growing internal organs or maintaining their function over prolonged time periods. For example, Japanese Patent No. 5881422 discloses methods of performing perfusion culture of internal organs or tissues removed from a mammal, the method including removing a first internal organ or tissue along with a second internal organ or tissue connected thereto in a living organism, hanging the first internal organ or tissue by immobilizing the second internal organ or tissue, and perfusing perfusate through blood vessels of the first internal organ or tissue.

JP-A-2001-120261 discloses methods for obtaining human progenitor cells ex vivo by culturing human stem cells, human hematopoietic progenitor cells, or human stromal cells in a liquid culture medium which is replaced or perfused, either continuously or periodically and replenishing nutrients to the culture w % bile maintaining it under physiologically acceptable conditions.

Furthermore, JP-T-2013-510590 discloses that, for the purpose of growing or analyzing tissues and internal organs, bioreactors are constructed which includes a growth chamber with one or more inlets, outlets, sensors, internal organ attachment sites, and/or internal organ identifiers and have functions of monitoring and varying growth conditions, growing internal organs, optimizing functions, sterilization, providing growth environments, and tracking the origin of internal organs and tissue, in response to one or more factors.

SUMMARY OF THE INVENTION

Problems to be Solved by the Invention

These conventional culturing devices and methods, however, have a variety of problems as follows.

For example, making up for the drawback of the perfusion culture methods disclosed in Japanese Patent No. 5881422, the methods for culturing compositions containing human stem cells disclosed in JP-A-2001-120261 allow removal of waste matter eliminated from a living internal organ and allow culture over prolonged time periods while function of the internal organ is maintained, by circulating blood or a culture medium through the internal organ; however, these methods are focused on maintaining the function of the internal organs and they are insufficient to be used as a method for growing internal organs.

Moreover, in the methods for producing an internal organ in JP-T-2013-510590, the growth and differentiation of internal organs are disclosed; however, the only disclosure is that certain cytokine secretory cells, placed upstream, provide cytokines to the internal organ placed downstream. Therefore, these methods have a problem that they cannot be applied to cases that different cytokines (e.g., hormones or growth factors) are required depending on the internal organ's stage of growth.

The present invention has been made in view of the problems mentioned above, and it is an object of the present invention to provide systems for aging induction, control devices for aging induction, methods for controlling aging induction, and programs for controlling aging induction with which aging can be induced without the need to add cytokines at different stages of aging.

Means to Solve the Problems

In order to achieve such object, a system for aging induction according to the present invention includes: a first culture chamber for perfusing, with a culture medium, a subject of aging-induction, the subject of aging-induction being derived from a living organism; a second culture chamber for perfusing a secretor with a culture medium, the secretor secreting a cytokine; and a control device for aging induction including: a detection unit; a memory unit for storing a protocol for aging induction, the protocol defining a procedure for the aging induction; and a control unit including: an aging state detector for detecting, via the detection unit, an aging state of the subject of aging-induction; and a flow rate controller for controlling, based on the protocol for aging induction, a flow rate at which the culture medium containing the cytokine secreted by the secretor is supplied to the subject of aging-induction, according to the aging state of the subject of aging-induction.

In the system for aging induction mentioned above, the system for aging induction of the present invention is characterized by further including a third culture chamber for perfusing, with a culture medium, a secretor that secretes another cytokine, wherein the secretor in the second culture chamber is regarded as a subject of aging-induction, and a flow rate at which the culture medium containing the cytokine secreted by the secretor in the third culture chamber is supplied to the subject of aging-induction is also controlled with the flow rate controller.

In the system for aging induction mentioned above, the system for aging induction of the present invention is characterized by further including a fourth culture chamber for perfusing, with a culture medium, a secretor that secretes another cytokine, wherein based on the protocol for aging induction, a switching control is performed with the flow rate controller by switching from the cytokine secreted by the secretor in the second culture chamber to the cytokine secreted by the secretor in the fourth culture chamber and supplying the culture medium to the subject of aging-induction, according to the aging state of the subject of aging-induction.

In the system for aging induction mentioned above, the system for aging induction of the present invention is characterized in that the system is in fluid communication such that the culture medium with which the subject of aging-induction has been perfused in the first culture chamber is circulated to the other culture chamber(s) at least including the second culture chamber.

In the system for aging induction mentioned above, the system for aging induction of the present invention is characterized in that, with the flow rate controller, the subject of aging-induction in the first culture chamber is regarded as a secretor and a flow rate at which the culture medium containing the cytokine secreted by the secretor is supplied to the other culture chamber is controlled.

In the system for aging induction mentioned above, the system for aging induction of the present invention is characterized in that the flow rate is controlled via a valve provided to a flow path between the culture chambers with the flow rate controller.

In the system for aging induction mentioned above, the system for aging induction of the present invention is characterized in that the flow rate is controlled via a robot that moves liquid between the culture chambers with the flow rate controller.

In the system for aging induction mentioned above, the system for aging induction of the present invention is characterized in that the protocol for aging induction defines a procedure for inducing proliferation and/or differentiation of the subject of aging-induction.

In the system for aging induction mentioned above, the system for aging induction of the present invention is characterized in that the cytokine is a hormone, lymphokine, chemokine, monokine, myocaine, interleukin, interferon, hematopoietic factor, cell growth factor, tumor necrosis factor (TNF), adipokine, neurotrophic factor, antibody, humoral ligand, neurotransmitter, signaling molecule, chemotactic attractant and/or other humoral factors.

In the system for aging induction mentioned above, the system for aging induction of the present invention is characterized in that the subject of aging-induction and/or the secretor is/are a cell, tissue, or organ.

A control device for aging induction according to the present invention is connected at least to a first culture chamber for perfusing, with a culture medium, a subject of aging-induction, the subject of aging-induction being derived from a living organism, and a second culture chamber for perfusing, with a culture medium, a secretor that secrets a cytokine, and includes a memory unit for storing a protocol for aging induction, the protocol defining a procedure for the aging induction; a detection unit; and a control unit including: an aging state detector for detecting, via the detection unit, an aging state of the subject of aging-induction; and a flow rate controller for controlling, based on the protocol for aging induction, a flow rate at which the culture medium containing the cytokine secreted by the secretor is supplied to the subject of aging-induction, according to the aging state of the subject of aging-induction.

A method for controlling aging induction according to the present invention is executed by a computer connected at least to a first culture chamber for perfusing, with a culture medium, a subject of aging-induction, the subject of aging-induction being derived from a living organism, and a second culture chamber for perfusing, with a culture medium, a secretor that secrets a cytokine, the computer including: a memory unit for storing a protocol for aging induction, the protocol defining a procedure for the aging induction; a detection unit; and a control unit including: an aging state detector for detecting, via the detection unit, an aging state of the subject of aging-induction; and a flow rate controller for controlling, based on the protocol for aging induction, a flow rate at which the culture medium containing the cytokine secreted by the secretor is supplied to the subject of aging-induction, according to the aging state of the subject of aging-induction.

A program for controlling aging induction according to the present invention causes a computer to execute the following steps in a control unit, the computer being connected to at least a first culture chamber for perfusing, with a culture medium, a subject of aging-induction, the subject of aging-induction being derived from a living organism, and a second culture chamber for perfusing, with a culture medium, a secretor that secrets a cytokine, the computer including a memory unit, a detection unit, and the control unit, the memory unit for storing a protocol for aging induction, the protocol for aging induction, the protocol defining a procedure for the aging induction, the steps including: an aging state detection step for detecting, via the detection unit, an aging state of the subject of aging-induction; and a flow rate control step for controlling, based on the protocol for aging induction, a flow rate at which the culture medium containing the cytokine secreted by the secretor is supplied to the subject of aging-induction, according to the aging state of the subject of aging-induction.

Effect of the Invention

The present invention has an effect of inducing aging, while cutting the costs associated with adding cytokines at each stage of aging. More specifically, the present invention makes it possible to provide systems with which aging such as differentiation into an internal organ and proliferation of a subject of aging-induction can be induced by controlling the kind and amount of cytokines allowed to spread over the subject of aging-induction by co-culturing secretors such as a plurality of kinds of cells or tissues that secretes cytokines with the subject of aging-induction such as an internal organ to allow the subject of aging-induction to interact with the secretors, and to provide methods, devices, programs, recording media, and others therefor. Further, when cells are used as the subject of aging-induction, the present invention can be provided as a method for proliferating and differentiating cells that can be used for cellular therapies, and when tissue is used as the subject of aging-induction, the present invention can be provide as methods for growing/differentiating it into, for example, a sheet of cell tissue.

BRIEF DESCRIPTION OF THE DRAWINGS

FIG. 8A and FIG. 8B show examples of culture procedure data and position information of hormone-secreting cells;

FIGS. 11A and 11B show figures and tables showing examples of the culture procedure data and the position information of hormone-secreting cells in the illustrative example 2;

DETAILED DESCRIPTION OF THE INVENTION

A system and control device for aging induction, and a method and program for controlling aging induction according to the present embodiment of the present invention as well as an embodiment of a recording medium are described in detail below—with reference to the drawings. It should be noted that this invention is not limited to this embodiment. In particular, in the following embodiment culture chambers are connected to each other via tubes and one or more valves are configured to control the flow rates and switching of culture media flowing through the tubes, but the present invention is not limited thereto. For example, all culture chambers may be stand-alone and not connected to each other, with the control of the flow rates and switching being performed with a device such as a pipette robot that travels between or among culture chambers by delivering liquid between or among the culture chambers.

[Configuration of a System for Aging Induction]

Figure 1:
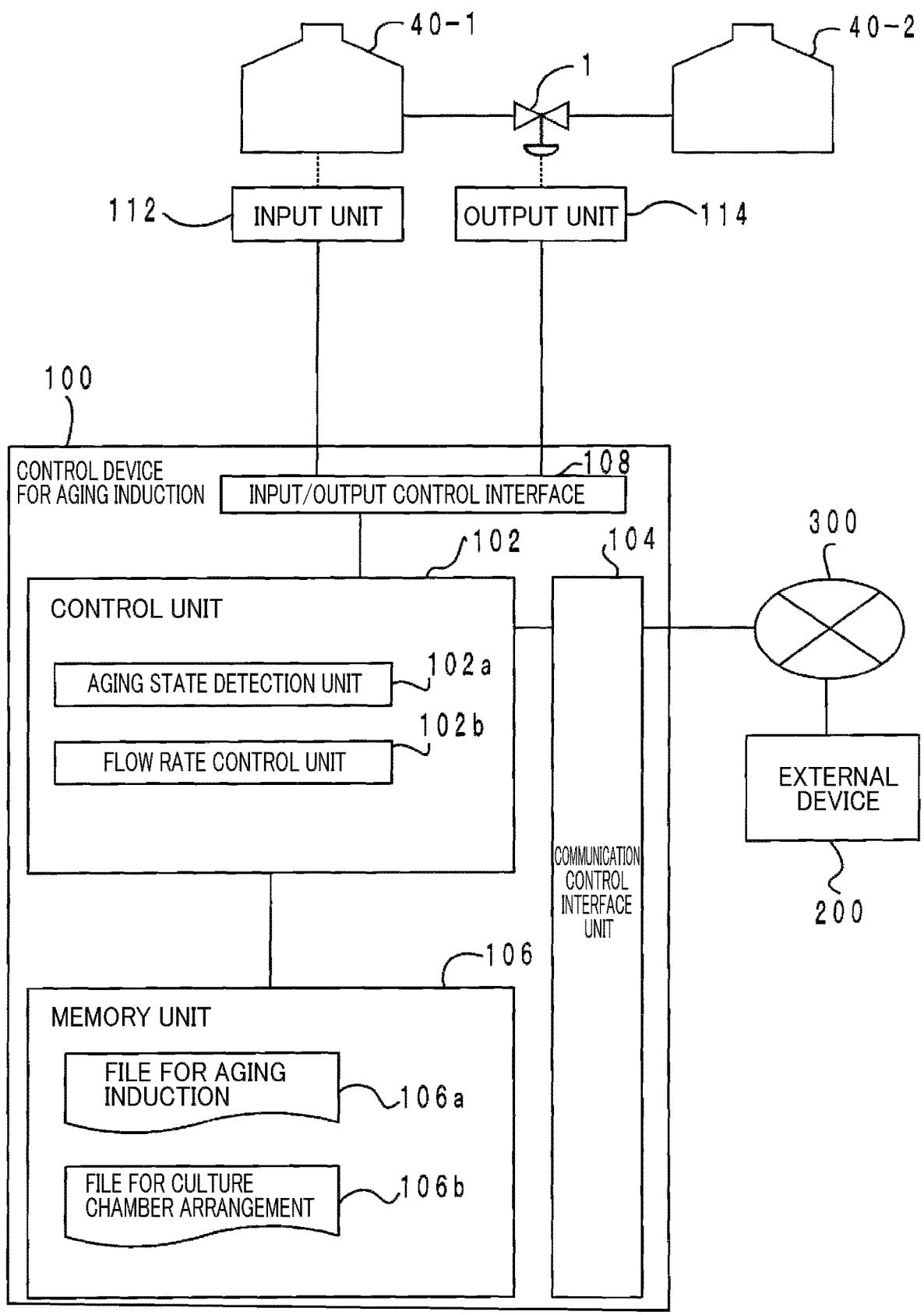
FIG. 1 is a configuration diagram showing an overall outline of a system for aging induction according to an embodiment of the present invention.

First, a configuration of a system for aging induction according to the present embodiment of the present invention is described below, and thereafter a process and others in the present embodiment are described in detail. FIG. 1 is a configuration diagram showing an overall outline of a system for aging induction according to an embodiment of the present invention.

As shown in FIG. 1, the system for aging induction of this embodiment is configured with a control device for aging induction 100 and at least two culture chambers 40.

In FIG. 1, the first culture chamber 40-1 is a culture chamber for perfusing, with a culture medium, a subject of aging-induction, the subject of aging-induction being derived from a living organism. As used herein, the subject of aging-induction may be a cell, tissue, an organ (an internal organ), etc. When the subject of aging-induction is a cell or tissue, perfusion may be performed by spreading the culture medium over a culture layer. Further, when the subject of aging-induction is an organ (an internal organ), perfusion may be performed by filling the blood vessels of the cultured internal organ with the culture medium. More specifically, a tube such as a cannula may be connected to a blood vessel in the internal organ etc. to culture it with inflows and outflows of the culture medium like blood flows. For circulation of the flow, separate culture medium circulation mechanisms may be provided for each culture chamber 40.

The second culture chamber 40-2 is a culture chamber for perfusing, with a culture medium, a secretor that secretes cytokines. The secretor may be a cell, a tissue, an organ (an internal organ), etc. Cytokines secreted by the secretor may be various kinds of hormones, lymphokines, chemokines, monokines, myocaines, interleukins (ILs), interferons (IFNs), hematopoietic factors (CSFs), cell growth factors, tumor necrosis factors (TNFs), adipokines, neurotrophic factors (NGFs), antibodies (e.g., agonist antibodies), humoral ligands, neurotransmitters, signaling molecules, chemotactic attractants, or other humoral factors involved in the aging of cells, tissues, organs (internal organs), etc. In this embodiment, the term "aging" includes proliferation, differentiation, apoptosis, necrosis, etc.

As shown in FIG. 1, in the present embodiment, the first and second culture chambers 40-1 and 40-2 are in fluid connection with each other via a tube having a valve 1 in a flow path and are configured such that the flow rate can be controlled by opening and closing the valve 1. As to the structure of the valve, a known valve of, for example, a flange or screw type can be used. For controlling the valve, it is possible to use a known regulating valve of, for example, a pneumatic, electric, or hydraulic type. Further, a check valve may be provided to prevent reverse flows.

Figure 2:
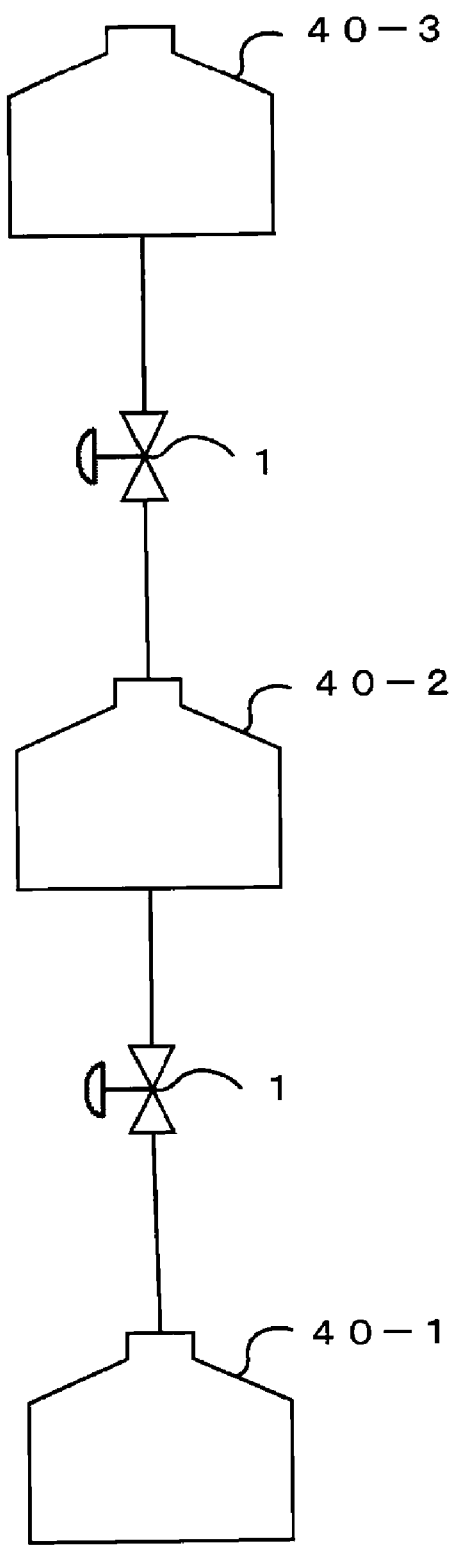
FIG. 2 is a diagram showing an example of a serial arrangement of culture chambers 40.

In FIG. 1, the system for aging induction is illustrated with two culture chambers 40, but the present invention is not limited thereto. Three or more culture chambers 40 may be connected in fluid communication with each other in series, in parallel, and/or in flow circulation. FIG. 2 is a diagram showing an example of a serial arrangement of the culture chambers 40.

For serial arrangements, as shown in FIG. 2, the system for aging induction further comprises, as an example, a third culture chamber 40-3 for perfusing, with a culture medium, a secretor that secretes a different kind of cytokines from those secreted by the secretor in the second culture chamber 40-2, and a control unit 102 (e.g., a flow rate control unit 102b) described later is also provided such that, with the secretor in the second culture chamber 40-2 being a subject of aging-induction, a flow rate at which the culture medium containing the cytokines secreted by the secretor in the third culture chamber 40-3 is supplied to the subject of aging-induction in the second culture chamber 40-2 can be controlled. In this manner, by controlling the flow rate at which the culture medium is delivered from the third culture chamber 40-3 to the second culture chamber 40-2, it is possible to induce aging such as proliferation and differentiation of the secretor in the second culture chamber 40-2 (which is a subject of aging-induction for the secretor in the third culture chamber 40-3) and thereby to change the level, kind, and the others of the cytokines secreted by the secretor in the second culture chamber 40-2; therefore, even at a fixed flow rate, it is possible to indirectly control the level and details of the effect of the cytokines supplied to the subject of aging-induction in the first culture chamber 40-1.

Figure 3:
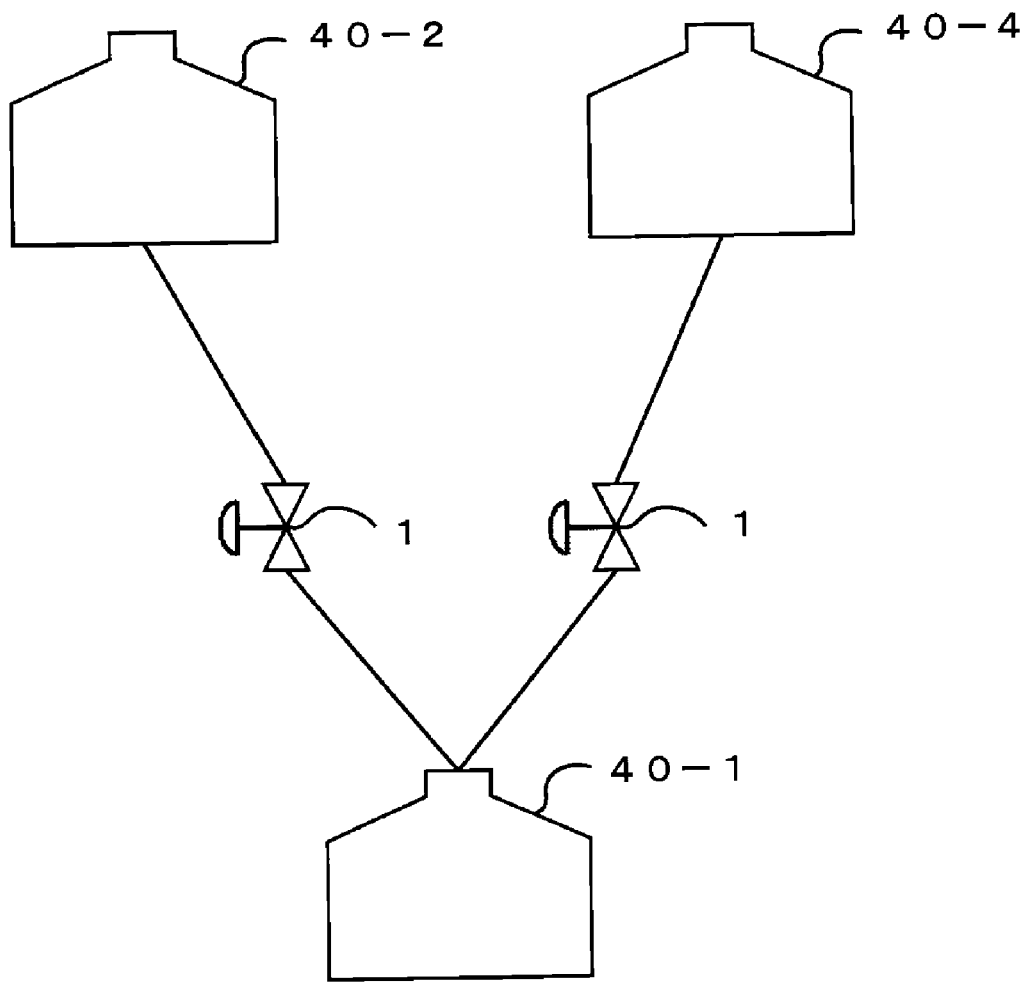
FIG. 3 is a diagram showing an example of a parallel arrangement of the culture chambers 40.

Here, FIG. 3 is a diagram showing an example of a parallel arrangement of the culture chambers 40.

For parallel arrangements, as shown in FIG. 3, the system for aging induction comprises, as an example, a fourth culture chamber 40-4 for perfusing, with a culture medium, a secretor that secretes a different kind of cytokines from those secreted by the secretor in the second culture chamber 40-2, and is configured such that the control unit 102 (e.g., the flow rate control unit 102b) described later can perform a switching control by switching from the cytokines secreted by the secretor in the second culture chamber 40-2 to the cytokines secreted by the secretor in the fourth culture chamber 40-4 and supplying the culture medium to the subject of aging-induction in the first culture chamber 40-1, according to the aging state of that the subject of aging-induction. In this manner, by performing the switching control from the second culture chamber 40-2 to the fourth culture chamber 40-4, it is possible to change the kind, the level of the effect, etc. of the cytokines supplied to the subject of aging-induction in the first culture chamber 40-1. Here, FIG. 4 is a diagram showing an example of a flow circulation arrangement of the culture chambers 40.

Figure 4:
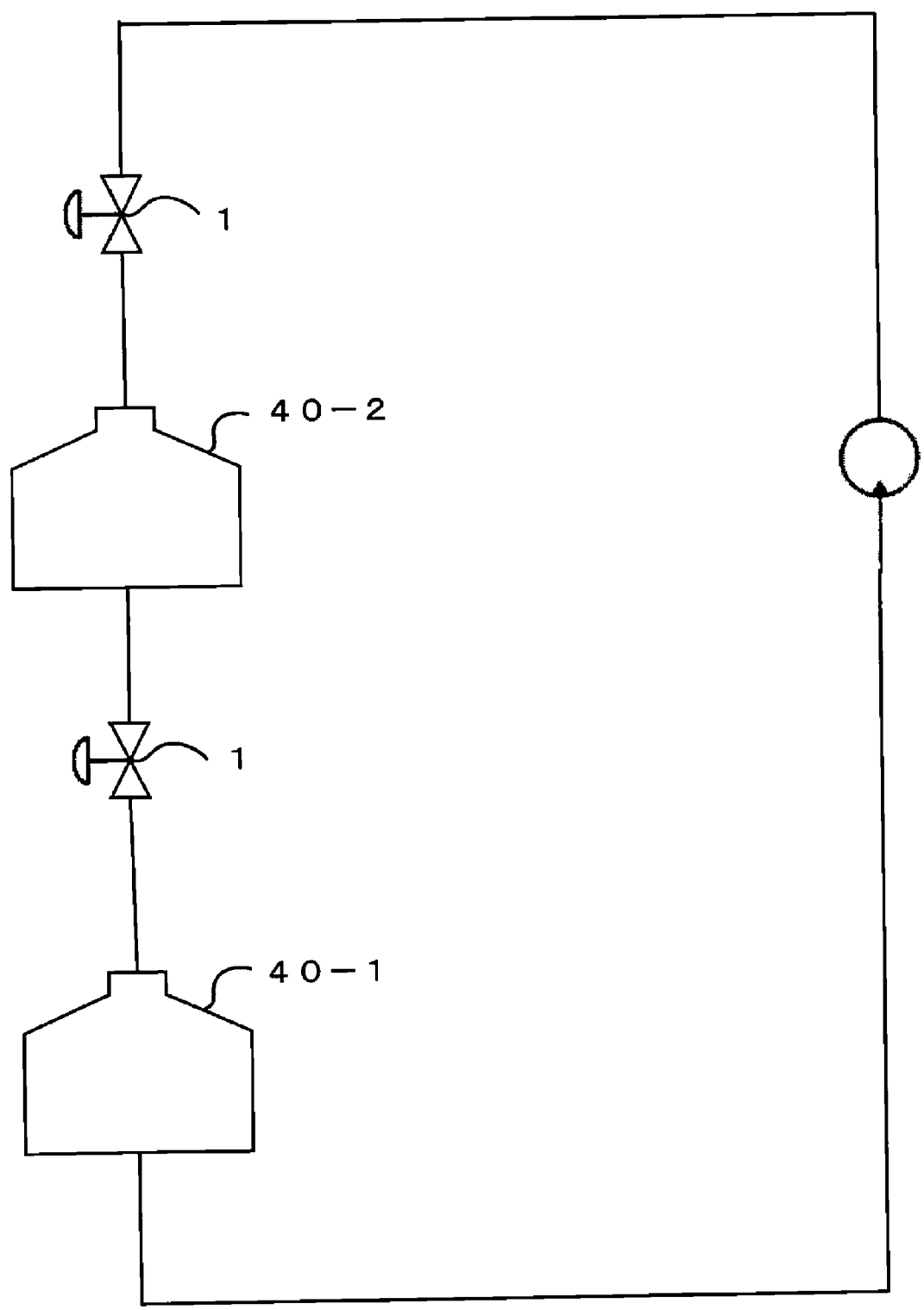
FIG. 4 is a diagram showing an example of a flow circulation arrangement of the culture chambers 40.

For flow circulation arrangements, as shown in FIG. 4, as an example, the chambers in the system for aging induction are joined such that the culture medium perfused to the subject of aging-induction in the first culture chamber 40-1 is circulated to other culture chamber 40 (such as the second culture chamber 40-2). The subject of aging-induction in the first culture chamber 40-1 secretes, as a secretor, cytokines and a culture medium may be supplied by perfusion to the secretor as a subject of aging-induction in another culture chamber such as the second culture chamber 40-2. In this manner, by the control of the flow rate in flow circulation from the first culture chamber 40-1 to the other culture chamber 40, aging such as proliferation or differentiation of the secretor in the second culture chamber 40-2 (the subject of aging-induction for the secretor in the first culture chamber 40-1) can be induced; therefore, it is possible to change the level and kind, etc. of the cytokines secreted by the secretor such as the second culture chamber 40-2 and, as a result, to indirectly control the level and details of the effect of the cytokines supplied to the subject of aging-induction in the first culture chamber 40-1.

It should be noted that two or more of the serial, parallel, and flow circulation arrangements mentioned above can be combined with any combination. For example, in the system for aging induction, the culture chambers 40 may be arranged in series in multiple stages; a parallel arrangement may be combined with a flow circulation arrangement; or the destination of supply, by flow circulation, of the culture medium containing the cytokines secreted by the secretor in the first culture chamber 40-1 may be controlled by switching. Although not shown, the valve(s) 1 and/or the flow path(s) may be provided with a filter function, a heat inactivation function, or various filters. Further, in the flow circulation system, a gas exchange unit and a dialysis unit may be provided. It should be noted that in the flow circulation system, a culture medium in a culture chamber 40 may be returned to the same culture chamber 40.

[Configuration of the Control Device for Aging Induction 100]

Returning back to FIG. 1, a configuration of the control device for aging induction 100 and other components of the present embodiment are described. As shown in the block diagram of FIG. 1, the configuration of the control device for aging induction 100 to which the present embodiment is applied shows only the part of the configuration related to this embodiment conceptually.

In FIG. 1, the control device for aging induction 100 is generally configured with the control unit 102 such as a CPU for unitarily controlling the entire control device for aging induction 100, a communication control interface unit 104 connected to a communication device (not shown) such as a router connected to, for example, a communication line, an input/output control interface unit 108 connected to an input unit 112 and an output unit 114 such as a sensor and a touch panel, and a memory unit 106 for storing various databases, tables, etc., and these units are communicatively connected via a freely-selected communication path or paths. The control device for aging induction 100 may be a microcomputer, a personal computer, a server computer, etc.

Various databases and tables stored in the memory unit 106 (e.g., a file for aging induction 106a and a file for culture chamber arrangement 106b) are storage means such as a small, fast memory (e.g., a cache memory) on, for example, a static random-access memory (SRAM) or a fixed disk device such as a hard disk drive (HDD) and a solid-state drive (SDD), and stores various programs, tables, files, databases, and the like used for various processes.

Among them, the file for aging induction 106a is storage means for information on aging induction for storing a protocol for aging induction defining a procedure for the aging induction. As an example, the protocol for aging induction may be stored in correlation with the kinds and thresholds for supply amounts of necessary cytokines according to, for example, stages of differentiation and phases of aging. The file for aging induction 106a may be configured as a database in which protocols for aging induction such as various culture procedure data are accumulated.

Further, the file for culture chamber arrangement 106b is storage means for arrangement information that stores arrangement information of the culture chambers 40. For example, the file for culture chamber arrangement 106b may store, for example, arrangement information such as parallel/serial/flow circulation arrangement(s) of the culture chambers 40, position information of the culture chambers 40 in which a cytokine secretor or a subject of aging-induction is contained, configuration information of the valves 1 and/or the tubes, and control information (e.g., a table for correspondence of flow rates and open/close signals).

In FIG. 2, the input/output control interface unit 108 controls the input unit 112 such as a sensor and a switch and the output unit 114. As the input unit 112, a sensor, a camera, an input device for opening and closing a valve that detect an aging state and others of the subject of aging-induction can be used. As the output unit 114, a device such as a valve opening/closing actuator and a pump can be used.

As the detection unit such as a sensor, the input unit 112 detects the state of the subject to be cultured such as cells, cell tissues, organs, or internal organs. For example, the input unit 112 such as a sensor detects an environment inside the culture chamber(s) 40 such as the state of internal organs. The input unit 112 may comprise a plurality of sensors.

In terms of the method of detecting the state of internal organs or the like, the internal organs or the like are known to secrete proteins, hormones or cytokines as signaling molecules representing a state at present. For example, the sensor of the input unit 112 detects the state of the internal organs by detecting these signaling molecules. More specifically, the sensor of the input unit 112 may detect, as a measure to sense the state of the internal organs or the like, pH, salt concentration, sodium ion concentration, potassium ion concentration, calcium ion concentration, temperature, sugar content, pressure, signaling molecule concentration, signaling protein concentration, and/or absorbance at a specific wavelength.

Enzyme-linked immunosorbent assay (ELISA) with use of antibodies or a spectrometer can be used as a method for detecting the concentration of signaling molecule transmitters or the concentration of signaling proteins. The ELISA determines the state of the subject of aging-induction by selectively detecting proteins or signaling molecules characteristic of the subject of aging-induction such as internal organs (see Japanese Patent No. 5881422). Since signaling molecules and signaling proteins have a high absorbance at wavelengths around 280 nm due to the aromatic amino acids that constitute them (see JP-A-2001-120261), the input unit 112 may detect the state of the subject of aging-induction by measuring the absorbance around $\lambda$abs.

In addition to the detection of the aging state mentioned above, the input unit 112 may also be provided with other input means such as a button, a lever, a touch panel, and a network device. Further, as the output unit 114, display means such as a liquid crystal monitor can be used besides the valve opening/closing actuator, the pump, or the like mentioned above.

Moreover, in FIG. 1, the control unit 102 is a processor such as a CPU which has an internal memory for storing a control program such as an operating system (OS), a program that defines various processing procedures and the like, and necessary data, and performs information processing for executing various processes using these programs etc. The control unit 102 is function-conceptually configured with an aging state detection unit 102$a$ and the flow rate control unit 102$b$.

Of these, the aging state detection unit 102$a$ is an aging state detector that detects the aging state of the subject of aging-induction via the input unit 112 as a detector (a sensor, etc.). For example, the aging state detection unit 102$a$ may quantify the concentration of signaling molecule transmitters of an antigen captured by the ELISA method based on the information detected by the sensor of the input unit 112. For another example, the aging state detection unit 102$a$ may quantify a protein having aromatic amino acids based on the absorbance near the excitation wavelength $\lambda$abs detected by the sensor of the input unit 112. Other than these, the aging state detection unit 102$a$ may perform morphological recognition based on microscopic image information taken via the input unit 112 such as a camera to judge the aging state such as a differentiation stage, a growth stage, or a development stage.

The flow rate control unit 102$b$ is a flow rate controller for controlling, based on the protocol for aging induction stored in the file for aging induction 106$a$, the flow rate at which the culture medium containing the cytokines secreted by the secretor is supplied to the subject of aging-induction, according to the aging state of the subject of aging-induction, detected by the aging state detection unit 102$a$. For example, the flow rate control unit 102$b$ may judge, according to an aging stage in the detected aging state of the subject of aging-induction, the kind and the level of the effect of the necessary cytokine by referring to the protocol for aging induction, and thereafter, perform a flow rate control or a switching control for the valves 1 via the output unit 114 to supply, to the subject to be aged, the culture medium containing the cytokines of the necessary kind and level of the effect, based on the arrangement information in the file for culture chamber arrangement 106$b$. It should be noted that the flow rate control unit 102$b$ may control a filter that blocks unnecessary cytokines or control the output unit 114 such that any unnecessary cytokines are inactivated with heat in order to prevent influence by humoral factors other than the necessary cytokines.

Here, the control device for aging induction 100 may be configured by being communicatively connected, via a network 300, to a database that provides the protocol for aging induction or an external device 200 that provides an external program and the others such as the program for controlling aging induction or an image morphology recognition program. In this case, the control device for aging induction 100 may be communicatively connected to the network 300 via a communication device such as a router and a wireless or wired communication line such as a leased line.

In FIG. 1, the communication control interface unit 104 is a device that performs communication control between the control device for aging induction 100 and the network 300 such as the Internet (or a communication device such as a router). That is, the communication control interface unit 104 has a function of communicating data with other terminals or stations via a communication line (whether wired or wireless is not important). The external device 200 is connected to the control device for aging induction 100 via the network 300, and has a function of providing an external database that provides, for example, a database that provides the protocol for aging induction to each terminal or a website or the like on which, for example, an external program such as the program for controlling aging induction or an image morphology recognition program is executed.

Here, the external device 200 may be realized by hardware elements such as a personal computer or a computer for a server and software elements such as an operating system, an application program and other data. For example, the external device 200 may be configured as, for example, a WEB server or an ASP server and the hardware may be configured by an information processing device such as a commercially available workstation or a personal computer and its associated devices. Further, each function of the external device 200 is realized by devices such as a processor such as a CPU, a disk device, a memory device, an input device, an output device, a communication control device in the hardware configuration of the external device 200 and a program for controlling them.

This concludes the description of each configuration of the system for aging induction of the present embodiment [Processing for Controlling Aging Induction]

Figure 5:
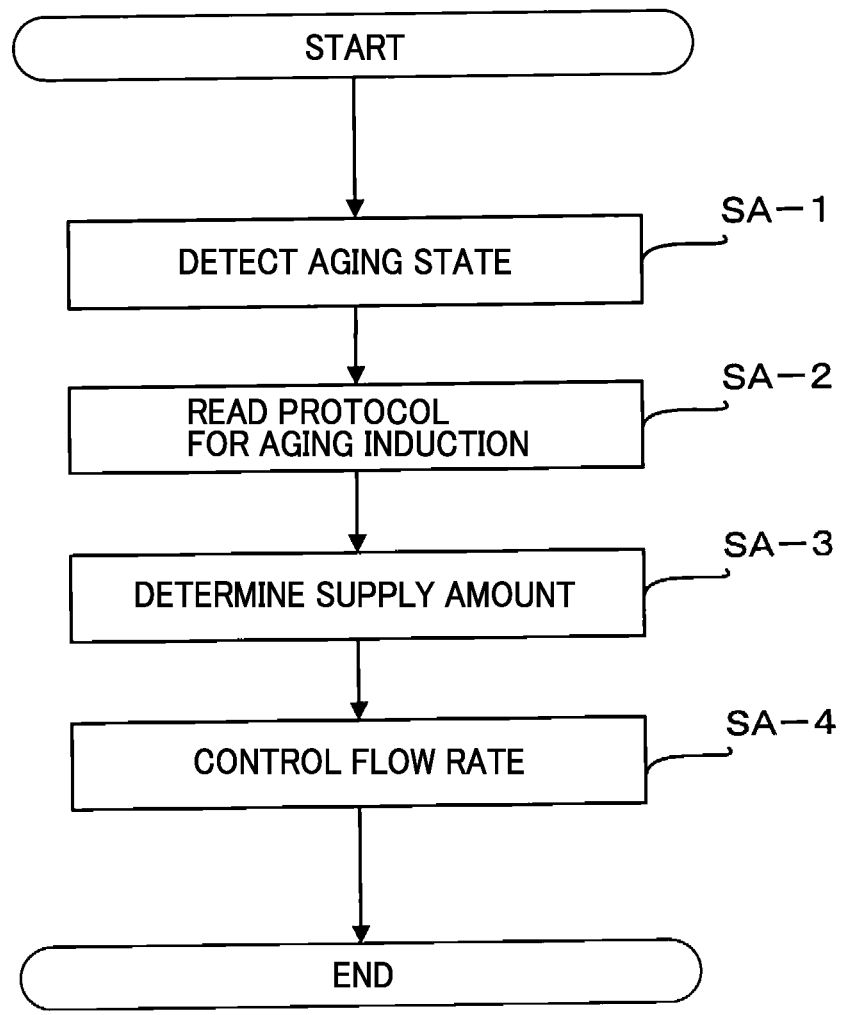
FIG. 5 is a flowchart showing an example of a process for controlling aging induction performed by a control device for aging induction 100 in a system for aging induction according to the present embodiment.

Next, an example of processing for controlling aging induction performed by the control device for aging induction 100 in the system for aging induction of the present embodiment configured as mentioned above is described below in detail with reference to FIG. 5. FIG. 5 is a flowchart showing an example of processing for controlling aging induction performed by the control device for aging induction 100 in the system for aging induction of the present embodiment.

First, the aging state detection unit 102$a$ detects an aging state of the subject of aging-induction in the culture chamber 40 via the input unit 112 such as a sensor and a camera (step SA-1). For example, the aging state detection unit 102$a$ may judge the aging state of the subject of aging-induction such as an internal organ by detecting, for example, pH, salt concentration, sodium ion concentration, potassium ion concentration, calcium ion concentration, temperature, sugar content, pressure, signaling molecule concentration, signaling protein concentration, and/or absorbance at a specific wavelength, via the input unit 112. For example, the aging state detection unit 102a may judge the aging state based on the presence or amount of antigen captured by antibody using the ELISA method, may judge the aging state by quantifying the amount of proteins based on the absorbance at the specific wavelength of 280 nm due to the aromatic amino acids, or may judge the aging state by performing morphological recognition based on an image taken using, for example, a camera.

Then, the flow rate control unit 102b reads the protocol for aging induction stored in the file for aging induction 106a (step SA-2). For example, the flow rate control unit 102b may retrieve a protocol for aging induction for the subject of aging-induction from the database containing protocols for aging induction.

Then, the flow rate control unit 102b refers to the read protocol for aging induction and determines the supply amount of the culture medium containing the cytokines, according to the aging state of the subject of aging-induction detected by the aging state detection unit 102a (step SA-3). It should be noted that the flow rate control unit 102b does not need to determine the value of the supply amount in a strict sense. For example, if the cytokine induces aging of a subject of aging-induction at a concentration equal to or higher than a threshold, the supply amount may be equal to or larger than the threshold. Further, even if no threshold data is included in the protocol for aging induction and the amount of cytokines contained in the culture medium is unknown, the flow rate control unit 102b can learn the level of the effect of the cytokines by correlating historical information on the supply amount by the valve opening/closing control to the change in aging state of the subject of aging-induction, judged by the aging state detection unit 102b as a result of the supply. Then, from the next time onward, by looking up a learning database, the flow rate control unit 102b may estimate the supply amount.

Subsequently, based on the arrangement information in the file for culture chamber arrangement 106b, the flow rate control unit 102b performs a flow rate control or a switching control for the valves 1 via the output unit 114 to supply, to the subject to be aged, the culture medium containing the necessary kind and level of the cytokines (step SA-4).

The above is an example of the processing for controlling aging induction performed by the control device for aging induction 100 in the system for aging induction of this embodiment. It should be noted that the control device for aging induction 100 may repeatedly perform the processes of the aforementioned steps SA-1 to SA-4.

Illustrative Examples

Hereinafter, various illustrative examples of the embodiment according to the present invention are described.

The present embodiment of the present invention provides a system, device, method, and others for inducing aging such as proliferation and differentiation of a subject of aging-induction by culturing plural kinds of cells, tissues or internal organs that secrete cytokines and by allowing them to interact with each other. Further, embodiments of the present invention are directed to provide systems, devices, and others for controlling, when secreted cytokines act on another cytokine secretor, their order or for causing cytokines to act on a subject of aging-induction. Hereinafter, the present illustrative examples 1 to 8 are described with reference to the drawings.

Illustrative Example 1

Figure 6:
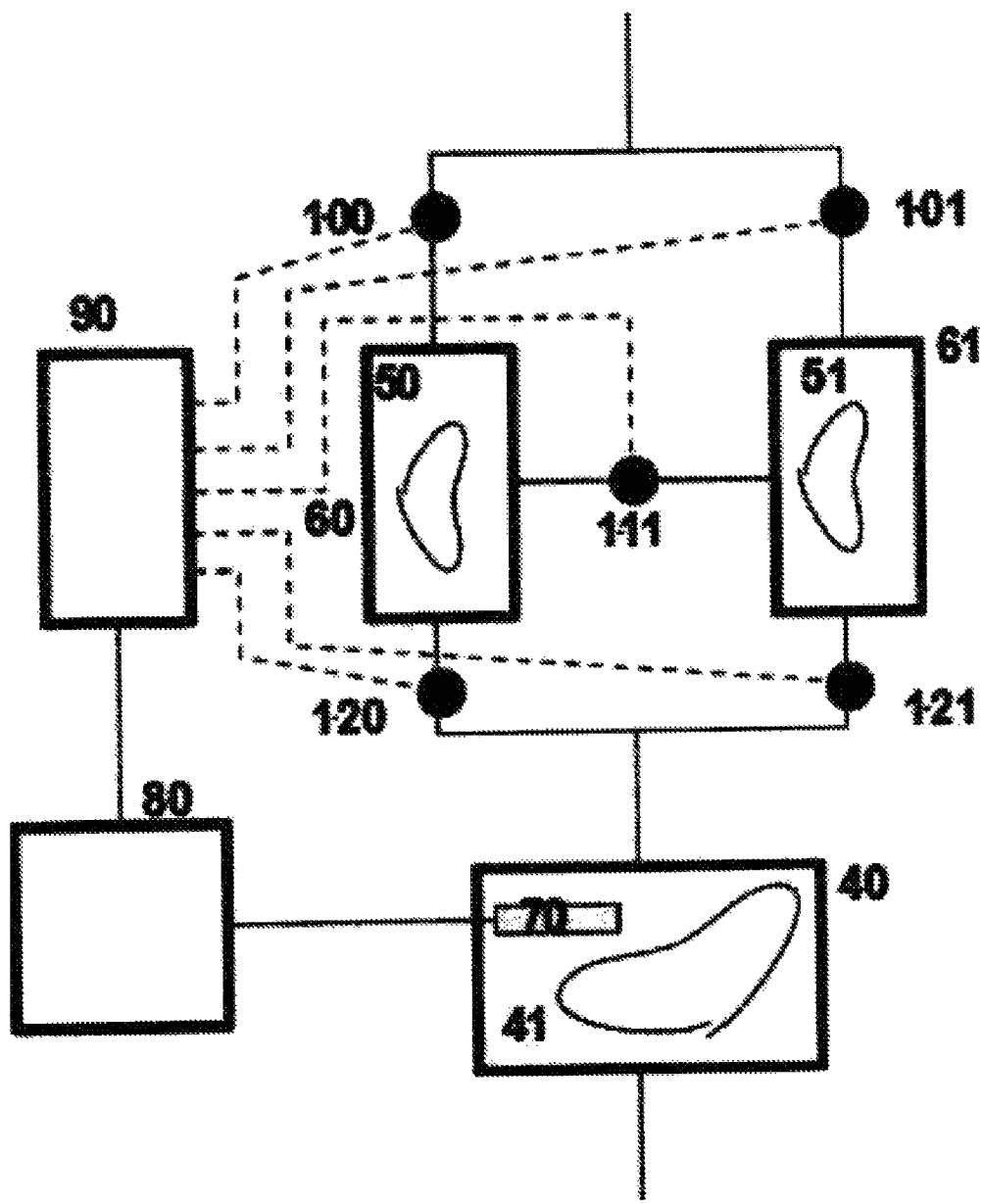
FIG. 6 is a diagram showing configurations of illustrative examples 1 and 2.

By using FIG. 6, an embodiment of a device for inducing aging of an internal organ of this illustrative example is described. A configuration diagram showing the illustrative example 1 of the present invention is shown in FIG. 6. FIG. 6 is a diagram showing configurations of the illustrative example 1 and the illustrative example 2.

A cell tissue 41 of the illustrative example 1 is a cell or a cell tissue or an internal organ, etc. which is a subject of aging-induction. The subject of aging-induction 41 may be a cell, a cell mass, an internal organ, a combination of two or more internal organs or others.

A vessel (culture chamber) 40 stores the subject of aging-induction 41 for culture. The vessel 40 has a size sufficient to store the subject of aging-induction 41 and protects the subject of aging-induction 41 from shock from and contact to outside. Further, the vessel 40 may have functions such as a light shielding property, impact resistance, and heat insulation property.

As a method of storing the subject of aging-induction 41 in the vessel 40, an internal organ may be perfused with a culture medium by connecting a culture medium inflow tube to an artery and an outflow tube to a vein. As a method of applying pressure to flow the culture medium in a desired direction, a method using a pump in a flow path, a method using gravity, a method using osmotic pressure, and the like can be contemplated. Besides, it may be supported by a known method such as by hanging it while covered by the diaphragm, as described in Japanese Patent No. 5881422.

A cytokine-secreting tissue container 60 stores a cytokine-secreting tissue 50. The cytokine-secreting tissue 50 may be a removed or cultured adrenal gland, thyroid gland, pituitary gland as well as cells having a function of secreting cytokines, into which genetically modified molecules have been introduced. As the kind of cytokines, examples include growth hormones and sex hormones, and as cytokines, epidermal growth factors (EGFs), fibroblast growth factors (FGFs), hepatocyte growth factors (HGFs) and chemokines.

Cytokines are added to the culture medium flowing in via a valve 1-00 or 1-11 in the cytokine-secreting tissue container 60 and the culture medium flows out via a valve 1-20.

Likewise, a cytokine-secreting tissue container 61 stores a cytokine-secreting tissue 51. The container 61 may be kept empty without the cytokine-secreting tissue 51 and used only as a flow path for the culture medium.

The valves 1-00, 1-01, 1-11, 1-20, and 1-21 control the flow rate(s) of the circulated culture medium. As to the structure of the valves, they may be driven by a physical force such as hydraulic pressure, air pressure, and hydraulic pressure, or an electromagnetic force may be used.

When the valves 1-00, 1-11, and 1-21 are opened and the valves 1-01 and 1-20 are closed, the flow path system is formed with a dialysis unit 30, the valve 1-00, the container 60, the valve 1-11, the container 61, valve 1-21, and the vessel 40 linked in this order.

When the valves 1-01, 1-11, and 1-20 are opened and the valves 1-00 and 1-21 are closed, the flow path system is formed with the dialysis unit 30, the valve 1-00, the container 61, the valve 1-11, the container 60, the valve 1-21, and the vessel 40 linked in this order; the places of the container 60 and the container 61 on the flow path are reversed from as compared to the previous example.

Further, when the valves 1-00 and 1-20 are opened and the valves 1-01, 1-11, and 1-21 are closed, only the container 60 is on the flow path system.

As a function of the input unit 112, a sensor 70 detects the environment inside the vessel 40 such as the state of the internal organ. The information on the state of the internal organ detected by the sensor 70 is transmitted to an input device 80 such as an input/output control interface 108 and supplied to a controlling device 90. It should be noted that a plurality of sensors may be provided.

Figure 7:
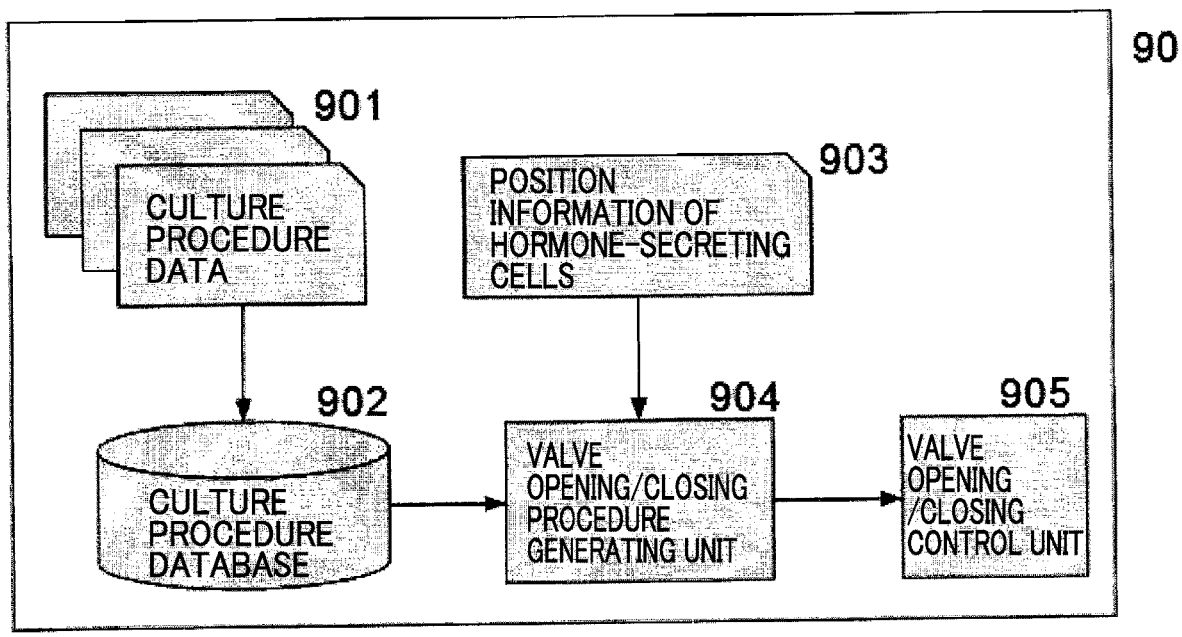
FIG. 7 is a system block diagram of a control unit device 90 of this illustrative example.
Figure 9:
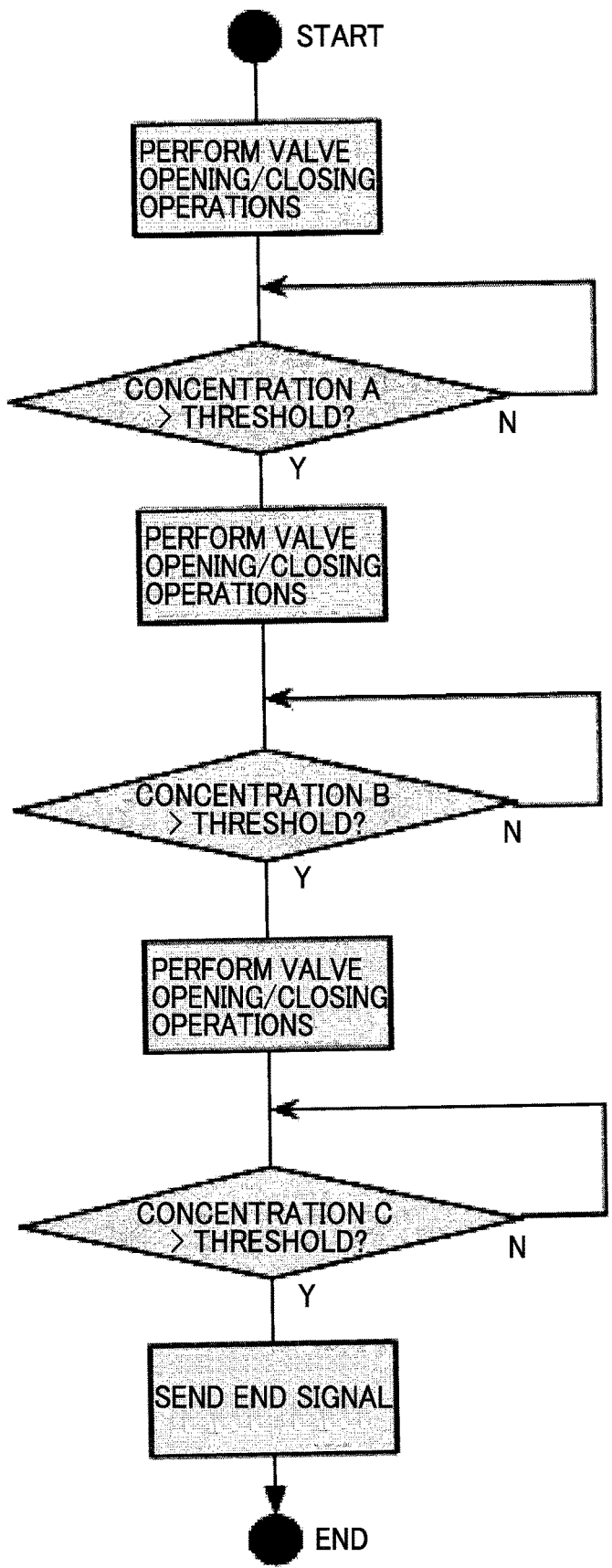
FIG. 9 is an example of a flowchart showing a procedure of valve opening/closing operations.

FIG. 7 is a system block diagram of the control unit device 90 of the present illustrative example. The controlling device 90 of the present illustrative example corresponds to the control unit 102 or the memory unit 106 of the aforementioned embodiment, includes a software shown in FIG. 7 or a system similar thereto, and controls opening and closing of the valves 1-00, 1-01, 1-11, 1-20, and 1-21 based on signals from the inputting device 80. FIG. 8 shows examples of culture procedure data and position information of hormone-secreting cells. FIG. 9 is an example of a flowchart showing a procedure of valve opening/closing operations.

The controlling device 90 of this illustrative example includes culture procedure data 901 and a culture procedure database 902 storing it, which correspond to the file for aging induction 106a of the aforementioned embodiment. Further, the controlling device 90 includes position information of hormone-secreting cells 903 (see FIG. 8) describing which cytokine-secreting tissue is stored in which container, which corresponds to the file for aging induction 106b in the aforementioned embodiment.

Figure 10:
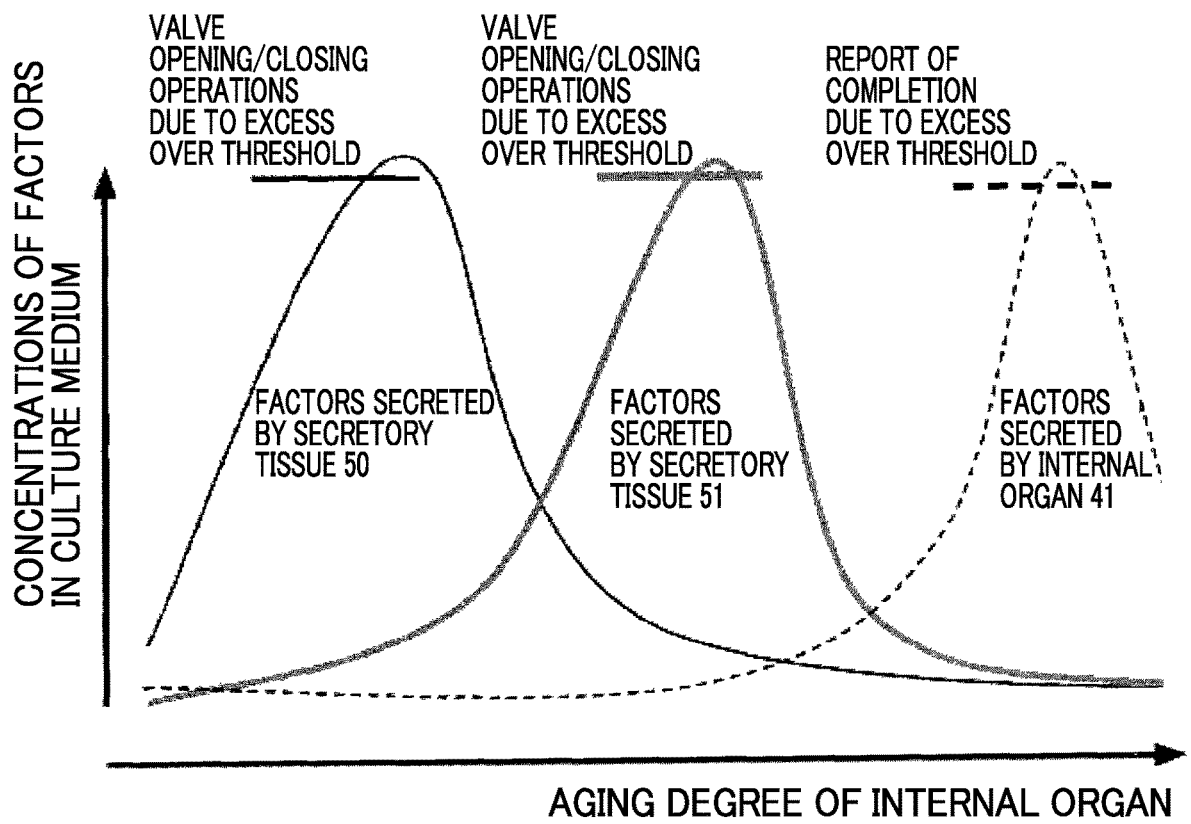
FIG. 10 is a graph showing concentrations of the factors in a culture medium in an aging process of an internal organ, when the internal organ is cultured using the present embodiment and the opening and closing operations of the valves are performed in the process.

The controlling device 90 also includes a valve opening/closing procedure generating unit 904 (see FIG. 9, corresponding to the flow rate control unit 102b mentioned above) for generating a manual of valve opening/closing operations from the culture procedure database 902 and position information of hormone-secreting cells 903 and a valve opening/closing control unit 905 (corresponding to the flow rate control unit 102b mentioned above) for performing opening and closing operations of the valves 1-00, 1-01, 1-11, 1-20, and 1-21 according to the manual of valve opening/closing operations. Various mechanisms such as those using electric signals, wireless, or mechanical actions can be contemplated as means for controlling opening and closing of the valves. FIG. 10 is a graph showing concentrations of each factor in culture media in an aging process of an internal organ, when the internal organ is cultured using this embodiment and the opening and closing operations of the valves are performed in the process.

Based on the above configuration and its dynamics, the cell tissue 41 undergoes chemical exposure of cytokines at time-varying concentrations as shown in FIG. 10, and the aging and differentiation of the cell tissue 41 are controlled.

Illustrative Example 2

In the illustrative example 2, using the configuration of the illustrative example 1 (see FIG. 6), an embodiment of the present invention in the case of aging muscle tissue in the vessel 40 is described with reference to a flowchart, with placental cells being denoted by 50, hepatic cells by 51, and myoblasts as the subject of aging-induction 41.

In JP-T-2013-510590, growth factors HGF secreted by placental cells act on hepatic cells to cause them to divide and differentiate. Furthermore, in JP-T-2008-513013, it has been reported that factors secreted by hepatic cells act on myoblasts and cause them to proliferate in an undifferentiated state; later, this factor was reported to be TGFβ (see Japanese Patent No. 5797113).

Based on this, in this experiment, the placenta, liver, and myoblasts were collected from mouse fetuses on the 12.5th day of pregnancy, and were each cultured for 1 week in a culture medium which was MEMα supplemented with 10% FBS. During this, the culture supernatant of the placental cells 50 was transferred to the hepatic cells 51, and the culture supernatant of the hepatic cells 51 was transferred to the myoblasts 41. The treatment groups were determined according to the volume of the culture media transferred as: 50%, 25%, and 10% of the total and 0%, i.e., no transfer. Finally, the number of cells was counted separately according to the number of cultured cells or size. FIG. 11 shows tables showing examples of the culture procedure data and the position information of hormone-secreting cells in the illustrative example 2.

Figure 12:
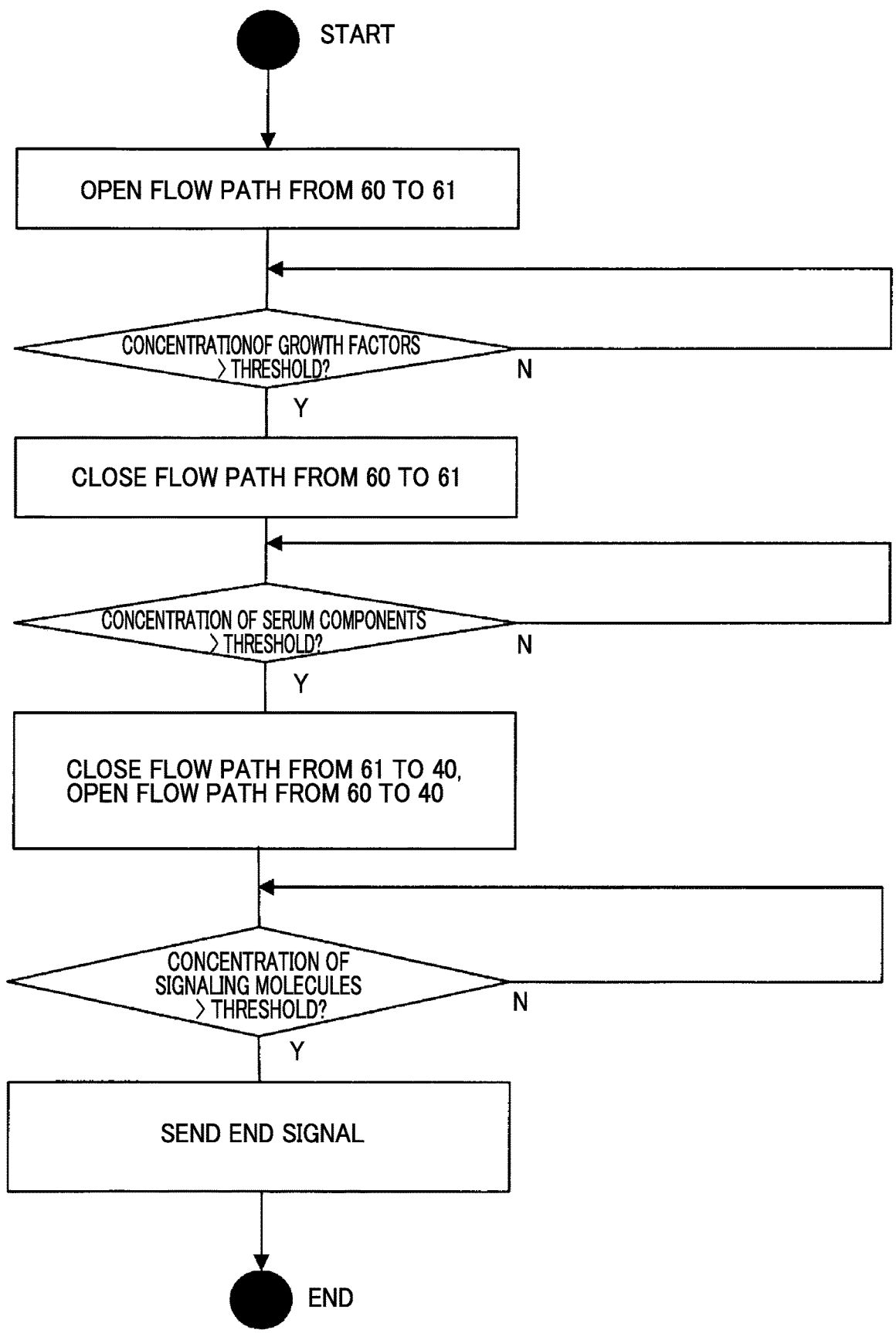
FIG. 12 is a diagram showing, as a flowchart, a manual of valve opening/closing operations.

As preparation for operating the device, the manual of valve opening/closing operations is generated by inputting the culture manual and the position information of hormone-secreting cells in FIG. 11. FIG. 12 is a flowchart showing the manual of valve opening/closing operations in this illustrative example.

When a culture operation starts according to the generated manual of valve opening/closing operations, the valves 1-00, 1-11, and 1-21 are opened and the valves 1-01 and 1-20 are closed in the initial state. In this configuration, the placental cells 50 are located upstream of the hepatic cells 51, and the growth factors secreted by the placental cells 50 act on the hepatic cells 51.

When the placental cells 50 proliferate to a certain extent and the sensor 70 detects the growth factors at a threshold value of 100 ng/mL or more, the valves 1-01 and 1-21 are opened and the valves 1-00, 1-11, and 1-20 are closed to shut off the flow path from the container 60 containing the placental cells 50 to the container 61 containing the hepatic cells. By this operation, only the container 61 remains on the flow path system, an appropriate amount of serum components is continuously supplied to the myoblasts 41, and the myoblasts 41 differentiate into muscle tissue.

Next, when the hepatic cells 51 further proliferate and the sensor 70 detects the serum components at a threshold value or more, the valves 1-00 and 1-20 are opened and the valves 1-01, 1-11, and 1-21 are closed to shut off the flow path from the container 61 containing the hepatic cells 51 to the vessel 40 containing the myoblasts 41. By this operation, the exposure of the serum components to the myoblasts 41 is stopped, and further differentiation of the myoblasts 41 into muscle tissue is stopped.

After that, if the muscle tissue differentiated from the myoblasts further grows and the sensor 70 detects that the concentration of the signaling molecules released by the muscle tissue exceeds the threshold value of 0.2 ng/L, it is judged that a sufficient volume of muscle tissue has been obtained, and the culture operation is terminated.

Figure 13:
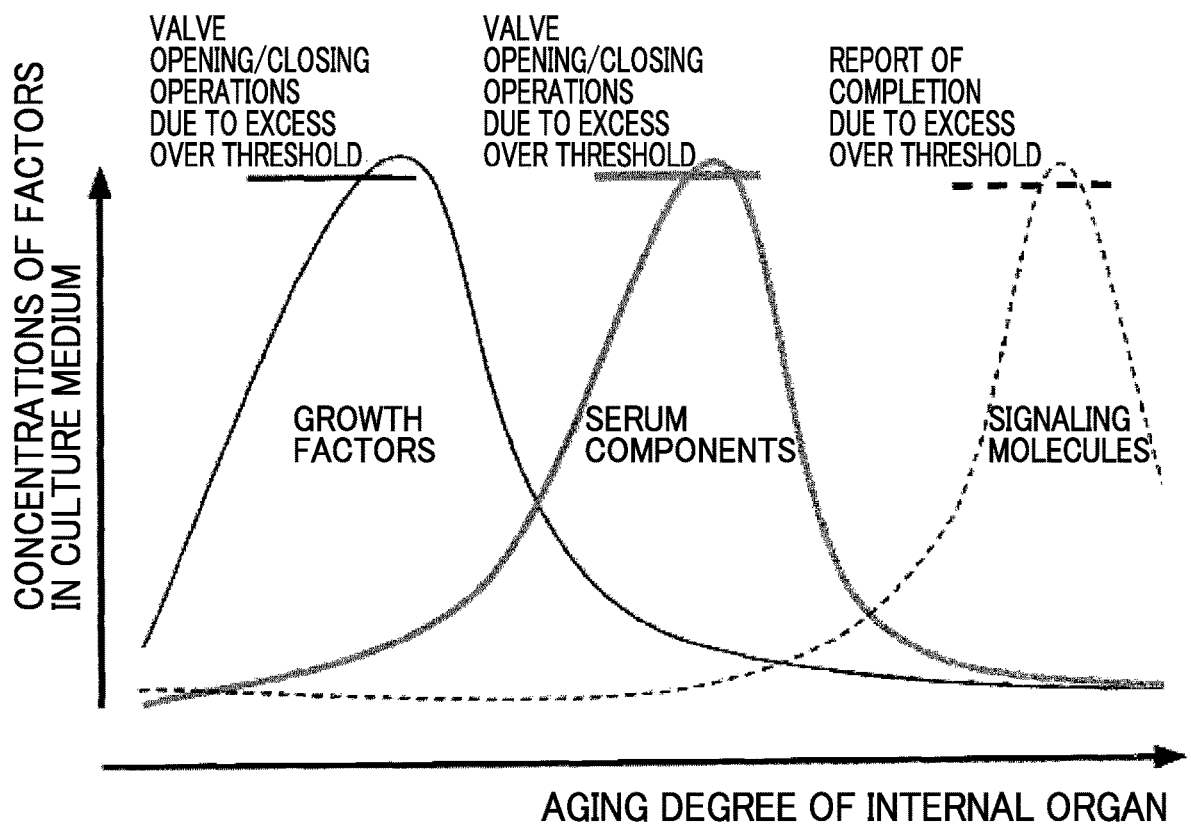
FIG. 13 is a graph showing changes of concentrations of each factor in a culture medium over time in a process of culturing myoblasts of the illustrative example 2.

During this series of operations, changes over time of the growth factors, the serum components, and the signaling molecules detected by the sensor 70 are as shown in FIG. 13. FIG. 13 is a graph showing the changes over time of the concentrations of each factor in the culture medium in the process of culturing the myoblasts of the illustrative example 2.

Figure 14A:
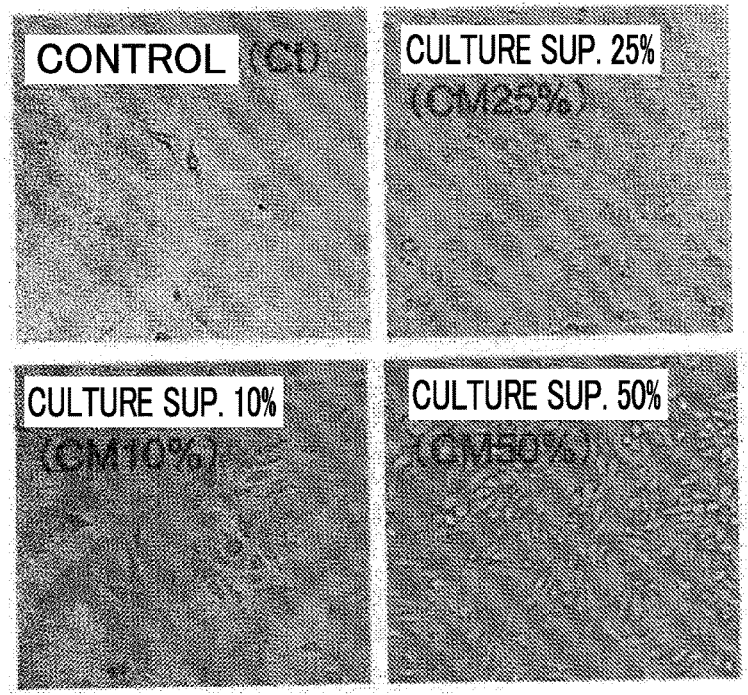
FIG. 14A and FIG. 14B are views showing the proliferation of hepatic cells with a supernatant of placental cell culture obtained as a result of the present illustrative example 2.
Figure 14B:
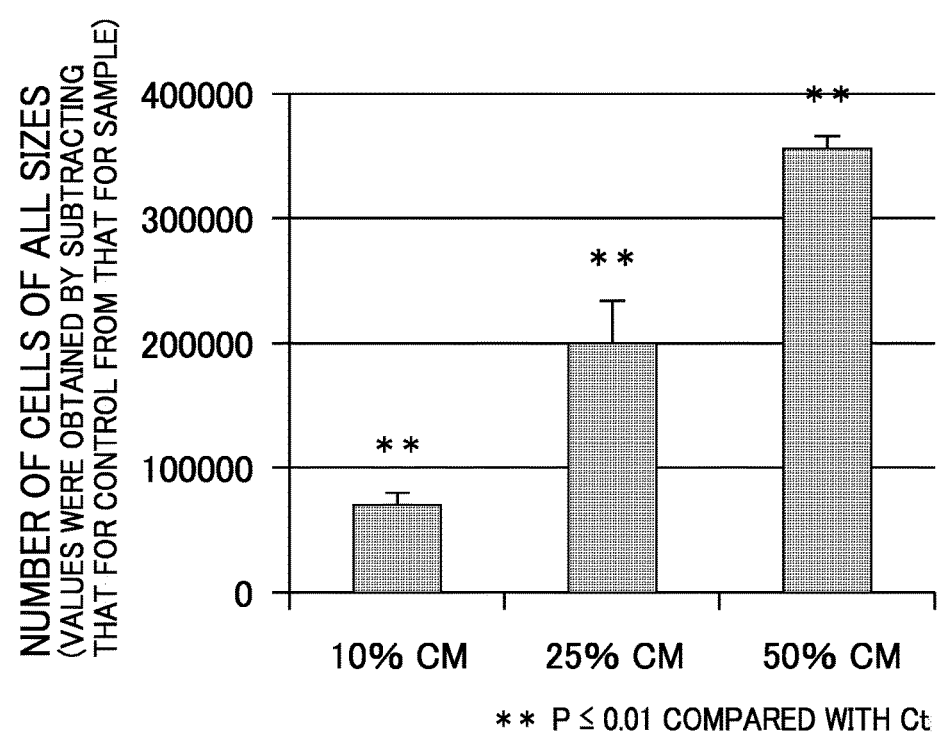
Figure 15A:
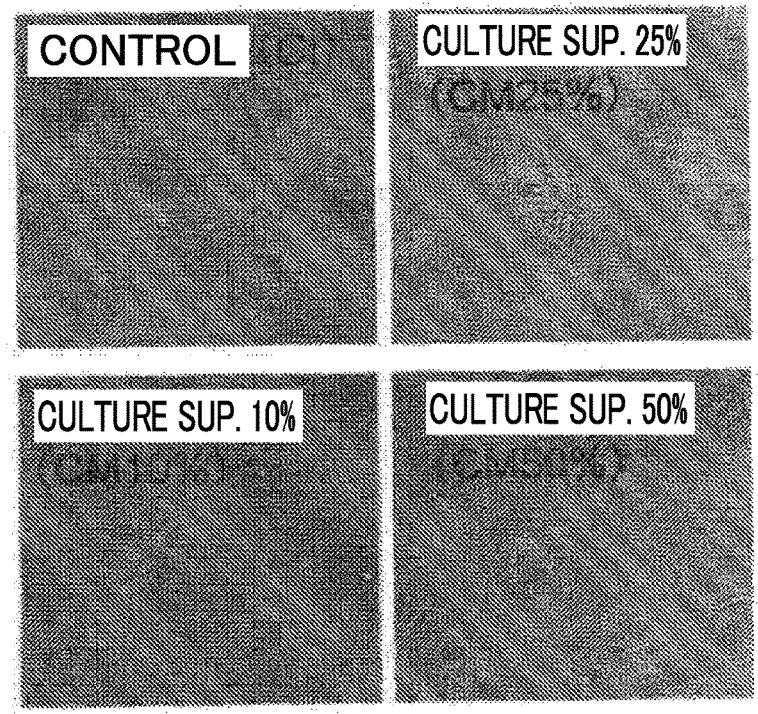
FIG. 15A and FIG. 15B are views showing the proliferation of myoblasts—with a supernatant of the hepatic cell culture.
Figure 15B:
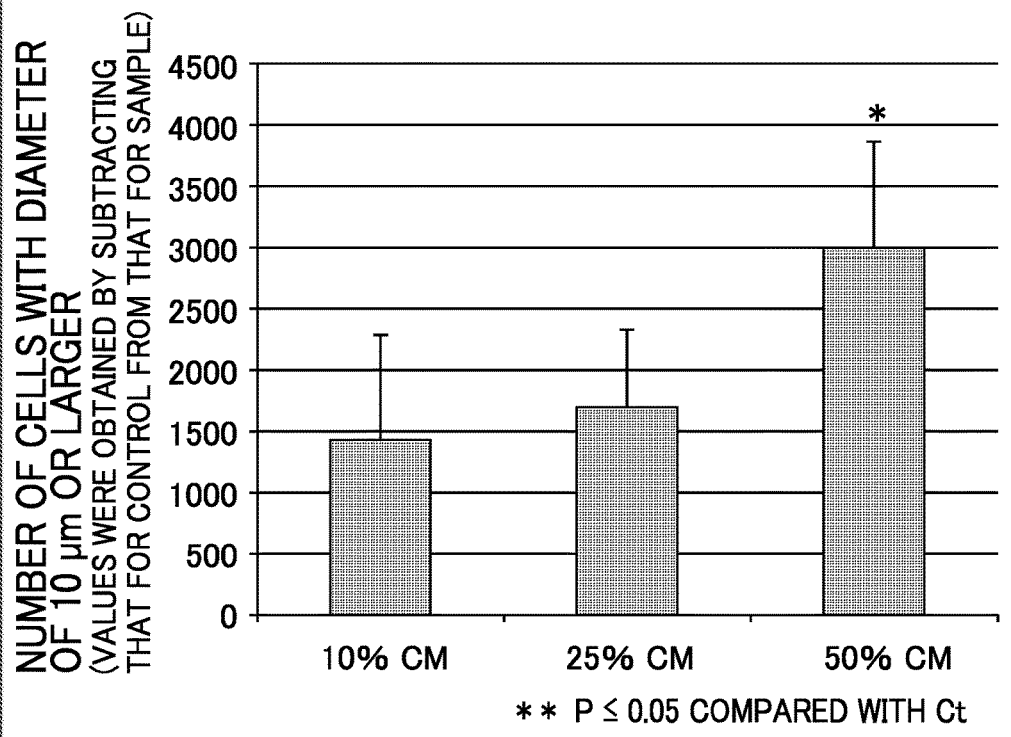

FIG. 14 is a view showing the proliferation of hepatic cells with the supernatant of the placental cell culture obtained as a result of this illustrative example 2, and FIG. 15 is a view showing the proliferation of myoblasts with the supernatant of the hepatic cell culture. As shown in FIGS. 14 and 15, according to this illustrative example, it was confirmed that the placental cells 50 act on the hepatic cells 51, the cells proliferate, the hepatic cells 51 act on the cell tissue 41, and the cells proliferate.

Illustrative Example 3

Figure 16:
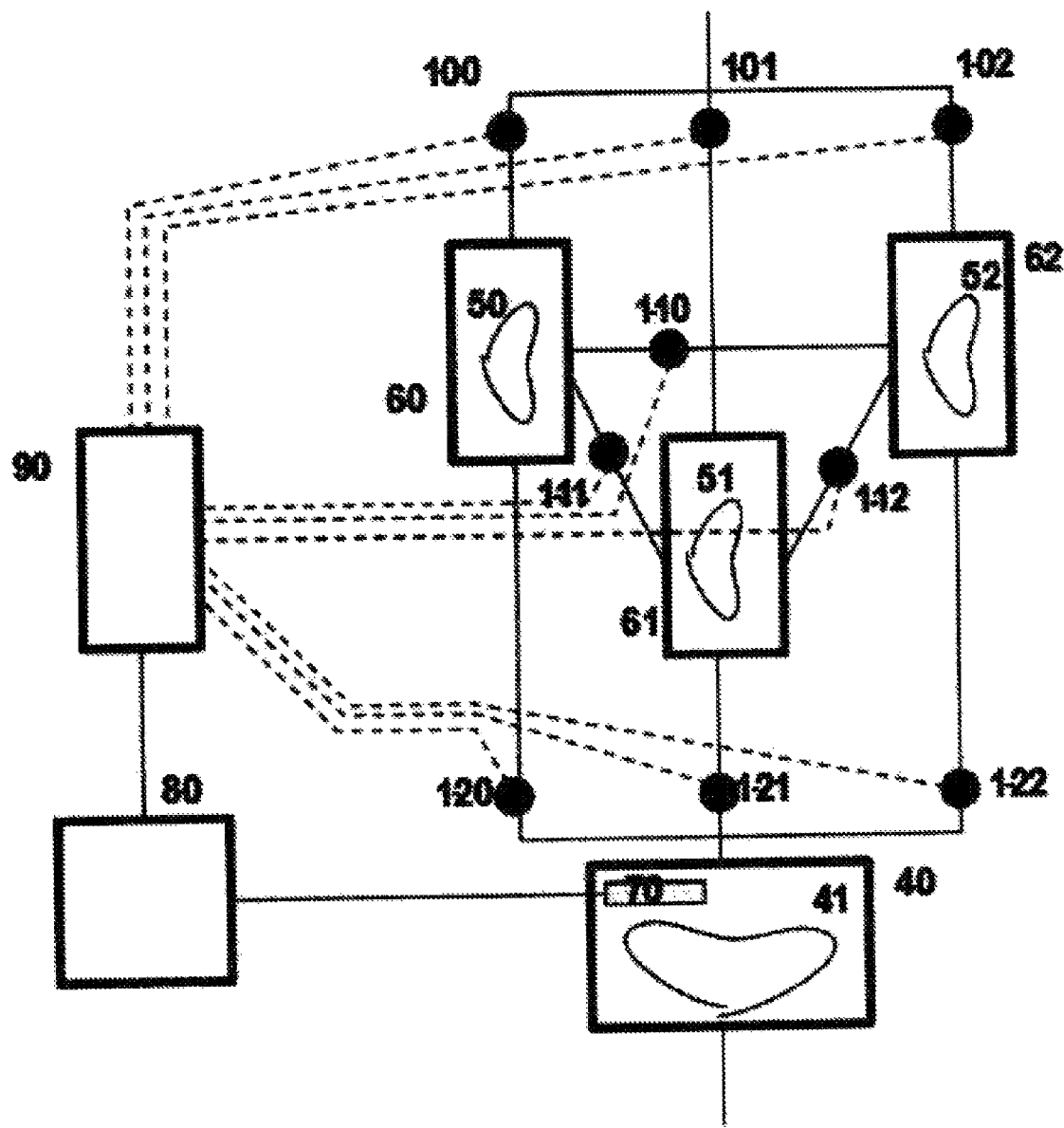
FIG. 16 is a configuration diagram of the illustrative example 3.

A configuration diagram showing the illustrative example 3 of this embodiment is shown in FIG. 16. FIG. 16 is the configuration diagram of the illustrative example 3. In this illustrative example, three kinds of cytokine-secreting tissues can be interacted.

For example, when the valves 1-00, 1-10, 1-12, and 1-21 are opened and the other valves 1-01, 1-02, 1-11, 1-20, and 1-22 are closed, the containers 60, 62, and 61 are linked in this order on the flow path system.

On the other hand, when the valves 1-01, 1-11, 1-10, and 1-22 are opened and the other valves 1-00, 1-02, 1-12, 1-20, and 1-21 are closed, the containers 61, 60, and 62 are linked in this order on the flow path system.

When the valves 1-02, 1-10, and 1-20 are opened, and the other valves 1-00, 1-01, 1-11, 1-12, 1-21, and 1-22 are closed, the containers 62 and 60 are linked in this order on the flow path system, and the container 61 is out of the flow path system. In this way, by opening and closing the valves to control the order in and constituent elements of the flow path system, the method of controlling the activity of cytokine-secreting tissues can be applied to a configuration in which four or more different kinds of cytokine-secreting tissues are stored in the same number of the containers, one kind for each.

Illustrative Example 4

Figure 17:
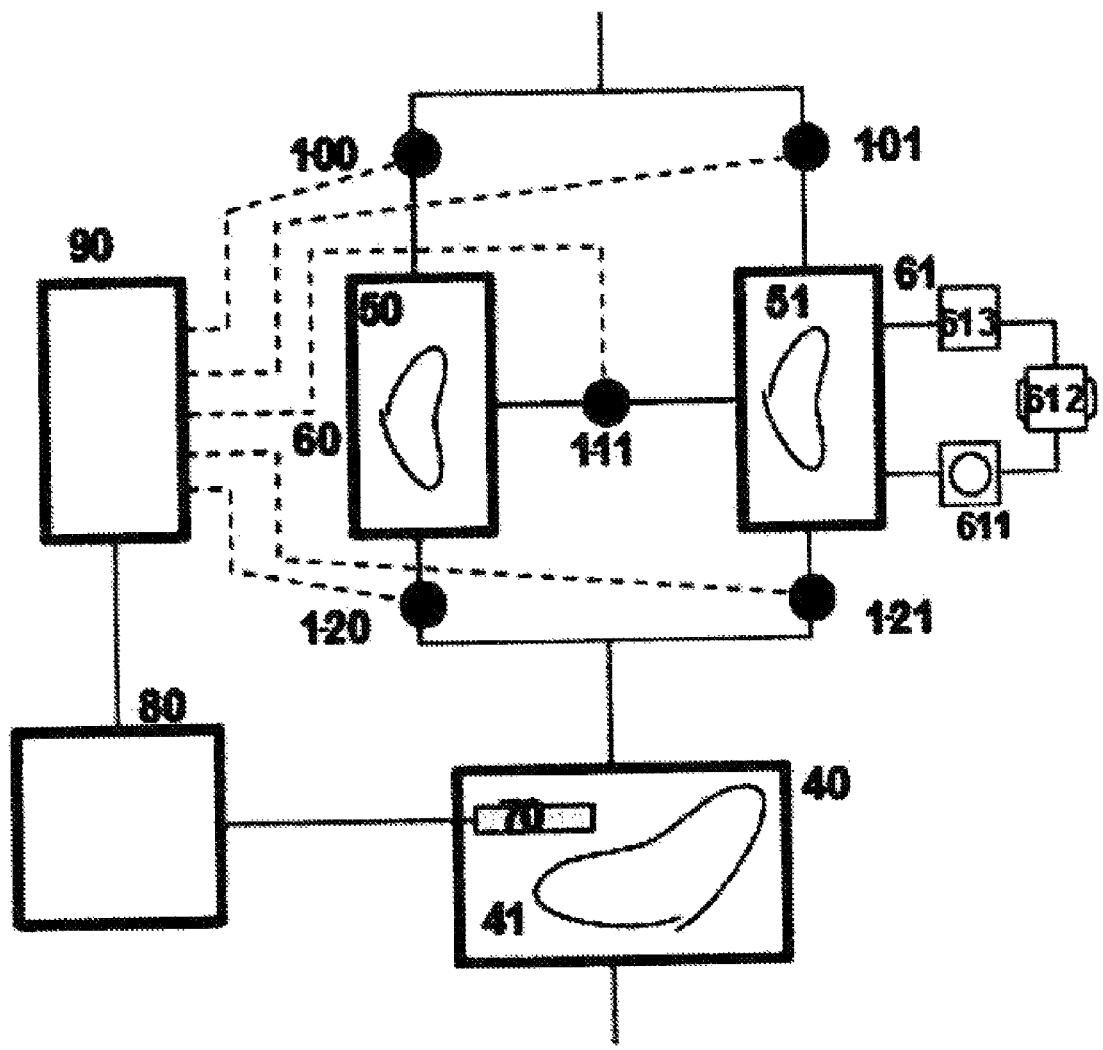
FIG. 17 is a configuration diagram of the illustrative example 4.

A configuration diagram of the illustrative example 4 of this embodiment is shown in FIG. 17. FIG. 17 is the configuration diagram of the illustrative example 4. In this illustrative example, provided is a way with which the cytokine-secreting tissues 50 and 51 or one of them are/is stored without being killed when either or both of the containers 60 and 61 is/are isolated from the flow path system by the operation of the valves 1-00, 1-01, 1-11, 1-20, and 1-21.

In this illustrative example, in addition to the first illustrative example shown in FIG. 1, the container 60 includes a flow path system composed of a pump 601, a gas exchange unit 602, and a dialysis unit 603.

For example, when the valves 1-01 and 1-21 are opened and the valves 1-00, 1-11, and 1-20 are closed, the container 61 is on a flow path system from the dialysis unit 30 to the vessel 40, but the container 60 is isolated. In this case, after the lapse of a long period of time, due to the activity of the cytokine-secreting tissue 50, the accumulation of waste matter and deficiency of oxygen and nutrients occur and the cytokine-secreting tissue 50 dies out. Accordingly, the life activity of the cytokine-secreting tissue 50 is maintained by circulating the culture medium using the pump 611, the gas exchange unit 612, and the dialysis unit 613.

By providing the container 60 with devices similar to the pump 611, the gas exchange unit 612, and the dialysis unit 613 for the container 61, it is possible to maintain the life activity of the cytokine-secreting tissue 50 even when the container 60 is isolated from the flow path system.

Illustrative Example 5

Figure 18:
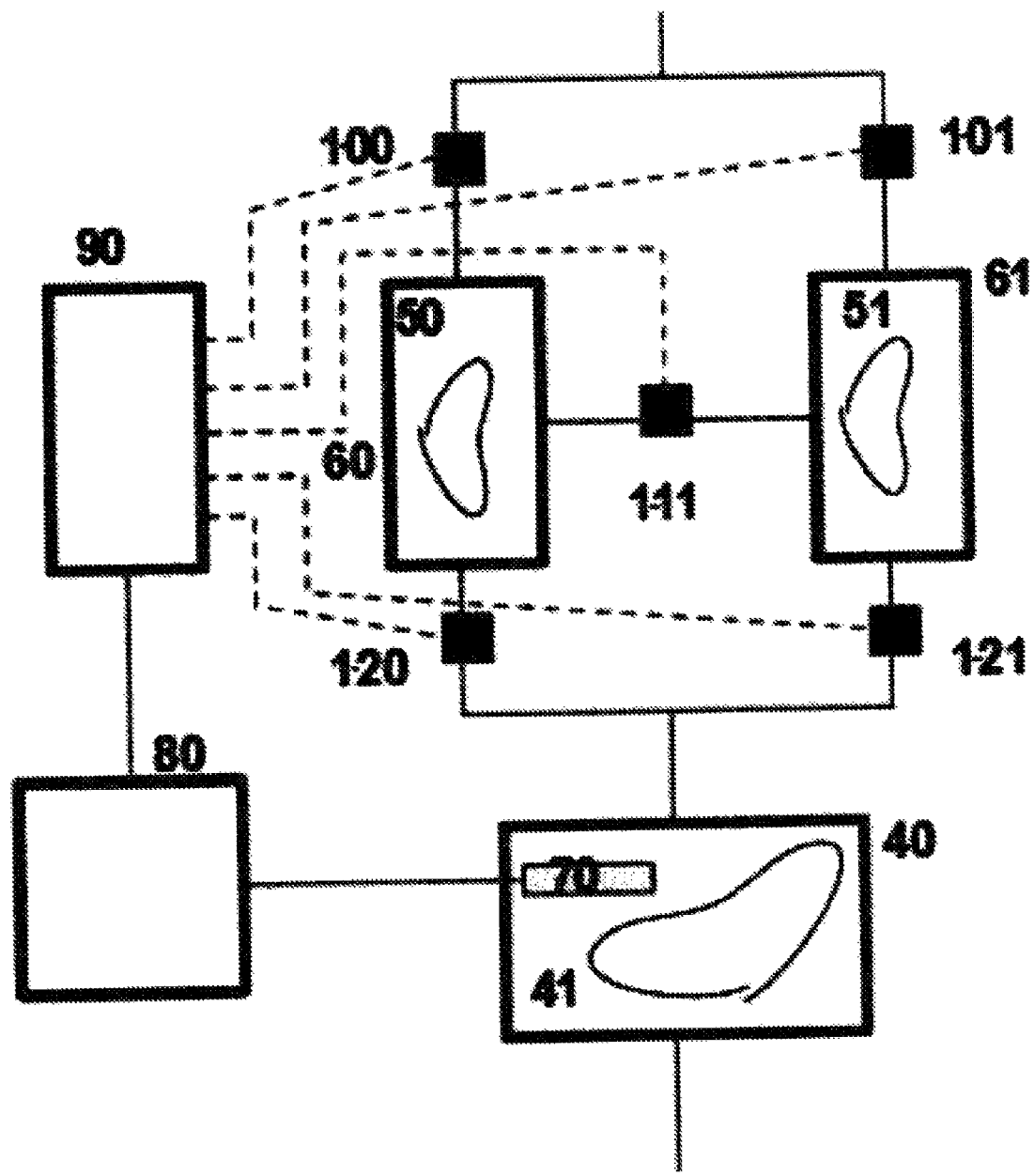
FIG. 18 are configuration diagrams of illustrative examples 5 and 6.

The illustrative example 5 provides a way of preventing entry of foreign matter such as bubbles, cells or cell debris or other dirt into the containers 60 and 61 and the vessel 40 as well as the flow paths connecting them shown in FIG. 1. FIG. 18 is a configuration diagram of the illustrative example 5 and the illustrative example 6.

For example, if foreign matter such as air bubbles and dirt intrude into the container 60, they adhere to the cells or tissue; consequently, the culture medium cannot reach that part of the cells, resulting in the deficiently of nutrients and drying. This causes local death of the cytokine secreting tissue 50. If cells or cells intrude, they cause clogging or adhesion in the cells or tissue, changing the character of the cells or tissue, or inducing their death.

In the present illustrative example, the valves 1-00, 1-01, 1-11, 1-20, and 1-21 have a mechanism such as a column, a filter, a trap or a branched flow to remove foreign matter. With this mechanism, foreign matter produced in, for example, the flow path system is removed by the valve 1-00 equipped with a mechanism for removing foreign matter before it flows into the container 60, and thus the cytokine-secreting tissue 50 can keep its life activity.

As the mechanism for removing foreign matter, filters, columns, and traps are clogged while they are used continuously and the flow path system is obstructed, so periodic cleaning is necessary. As means for eliminating the necessity of periodic cleaning, a cell sorter sold by, for example, BD or Beckman Coulter can be used or a sorting technique using a laminar flow disclosed in a patent (Japanese Patent No. 4601423 (Japanese Patent Application No. 2004-379327) owned On-chip Biotechnologies. Co., Ltd. can also be used.

Illustrative Example 6

The illustrative example 6 provides a way to remove components such as specific proteins or compounds from the containers 60 and 61, the vessel 40, and the flow paths connecting them shown in FIG. 1 or to neutralize their physiological effects.

In this illustrative example, the valves 1-00, 1-01, 1-11, 1-20, and 1-21 have a mechanism, such as a heating device, a UV irradiation device, a laser irradiation device, an injection device for a compound or a solution, for removing components such as specific proteins or compounds or for neutralizing their physiological effects. With this mechanism, it is possible to remove, by the valve 1-00, components such as specific proteins or compounds to be removed before they flow into, for example, the container 60.

For example, it has been reported that albumin, a serum component, secreted by the liver changes its characteristics rapidly and loses its physiological activity when its temperature exceeds around 60° C. On the other hand, casein, a milk protein, is relatively stable even at temperatures above 60° C. (Kato A, Osako Y, Matsudomia Y, Kobayashia K, "Changes in the Emulsifying and Foaming Properties of Proteins in Heat Denaturation", Agricultural and Biological Chemistry, 1983, 47:33-37, Japan Society for Bioscience, Biotechnology, and Agrochemistry). As described above, the thermal resistance differs from protein to protein depending on their structural properties, and these differences can be used to reduce the physiological effect of a specific protein.

Illustrative Example 7

Figure 19:
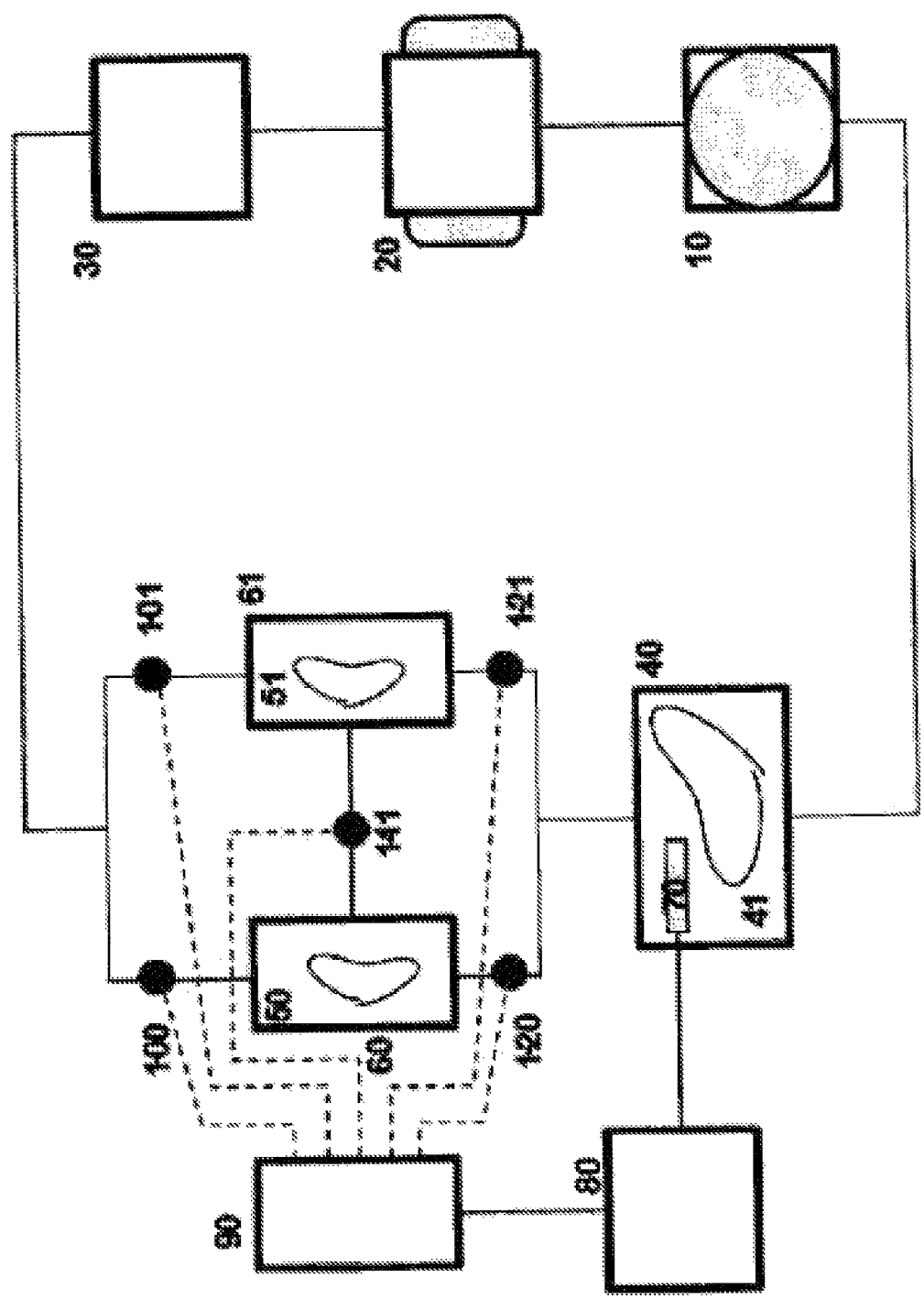
FIG. 19 is a configuration diagram of the illustrative example 7.

A configuration diagram showing the illustrative example 7 of the present invention is shown in FIG. 19. FIG. 19 is the configuration diagram of the illustrative example 7. In the illustrative example 7, a flow path system is annular and the culture medium is circulated and reused.

A pump 10 supplies pressure for circulating the culture medium from the internal organ container 40 toward a gas exchange unit 20. The pump may be a steady flow pump or a pulsatile pump, but a pulsatile pump is more preferable. Further, the position of the pump 10 may be determined anywhere on the flow paths connecting the gas exchange unit 20, the dialysis unit 30, and the vessel 40, such as between the gas exchange unit 20 and the dialysis unit 30 or between the container 60 and the vessel 40 for storage as long as a flow circulation pressure can be applied to the culture medium; or two or more pumps may be installed.

The gas exchange unit 20 removes carbon dioxide from the culture medium and adds oxygen. This function is equivalent to the oxygen/carbon dioxide exchange function used in artificial heart-lung devices etc.

The dialysis unit 30 removes waste matter from some or all of the incoming culture medium. As a removal method, a semipermeable membrane may be used, waste matter may be condensed and precipitated, or the culture medium may be replaced with a new one.

In this illustrative example, as the culture medium circulates, the interaction is iterated as shown in FIG. 19, and an effect of the substance secreted by the cell tissue 41 on the cytokine-secreting tissue 50 or 51 can also be obtained.

Figure 20:
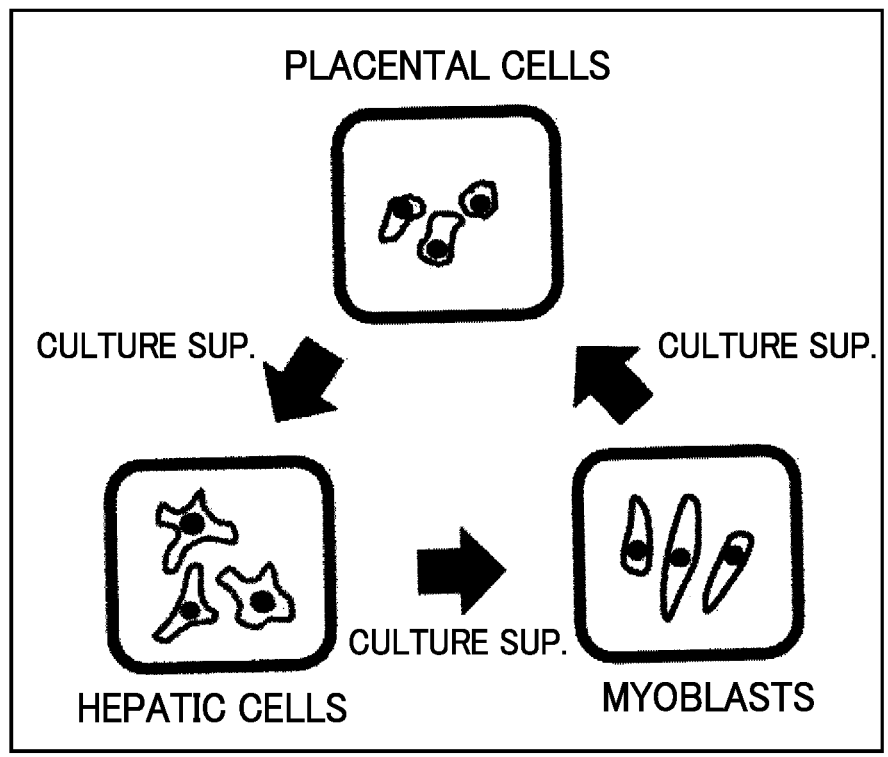
FIG. 20 is a diagram showing a closed chain of intercellular actions m the illustrative example 7.
Figure 21A:
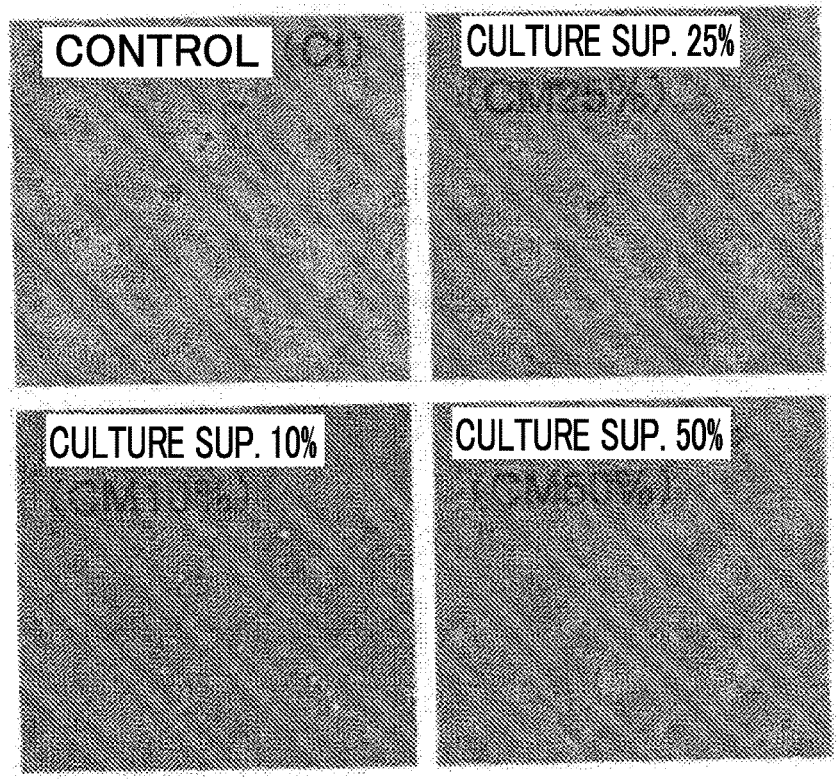
FIG. 21A and FIG. 21B are diagrams showing proliferation of placental cells with a supernatant of myoblasts according to this illustrative example 7.
Figure 21B:
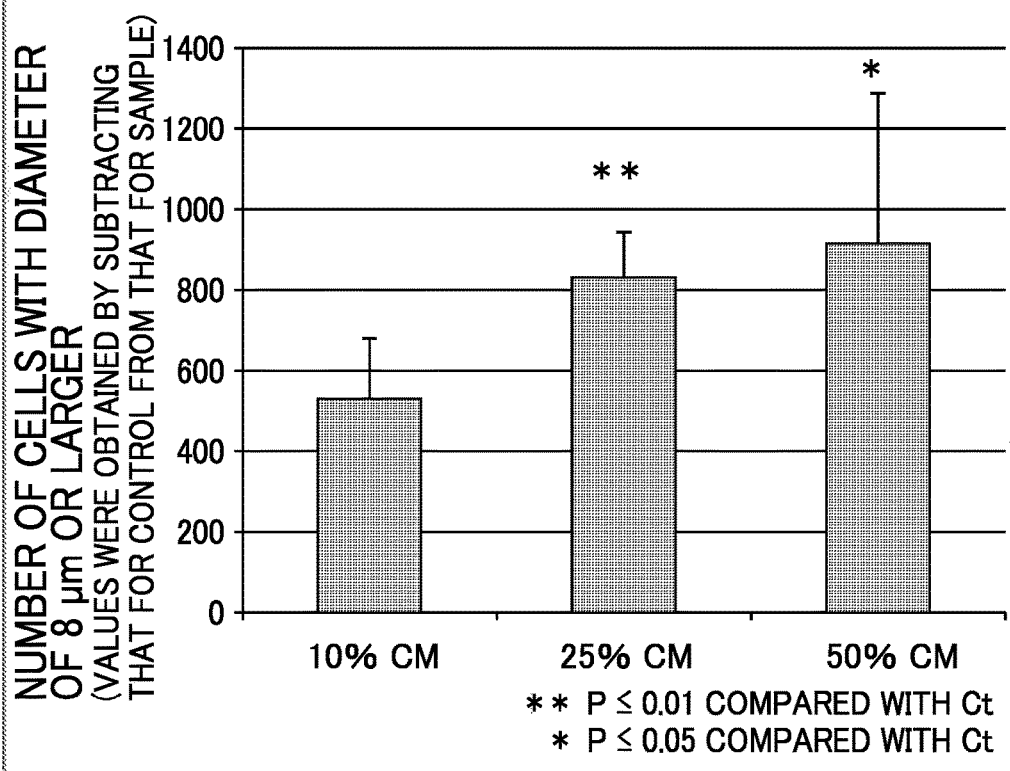

Here, FIG. 20 is a diagram showing a closed chain of intercellular actions in the illustrative example 7. FIG. 20 shows, when my cellular 41 is myoblasts and the cytokine-secreting tissue 50 is placental cells, a result of promoting the proliferation of placental cells by myoblasts. Here, it can be believed that EFG and FGF secreted by myoblasts act on placental cells. FIG. 21 is a diagram showing the proliferation of placental cells by a supernatant of myoblasts according to this illustrative example 7. As shown in FIG. 21, according to this illustrative example 7, it was found that desired cells or tissue can be obtained by circulating a culture medium containing a variety of cytokines using a flow circulation mechanism to interact the subject of aging-induction with it.

Illustrative Example 8

Figure 22:
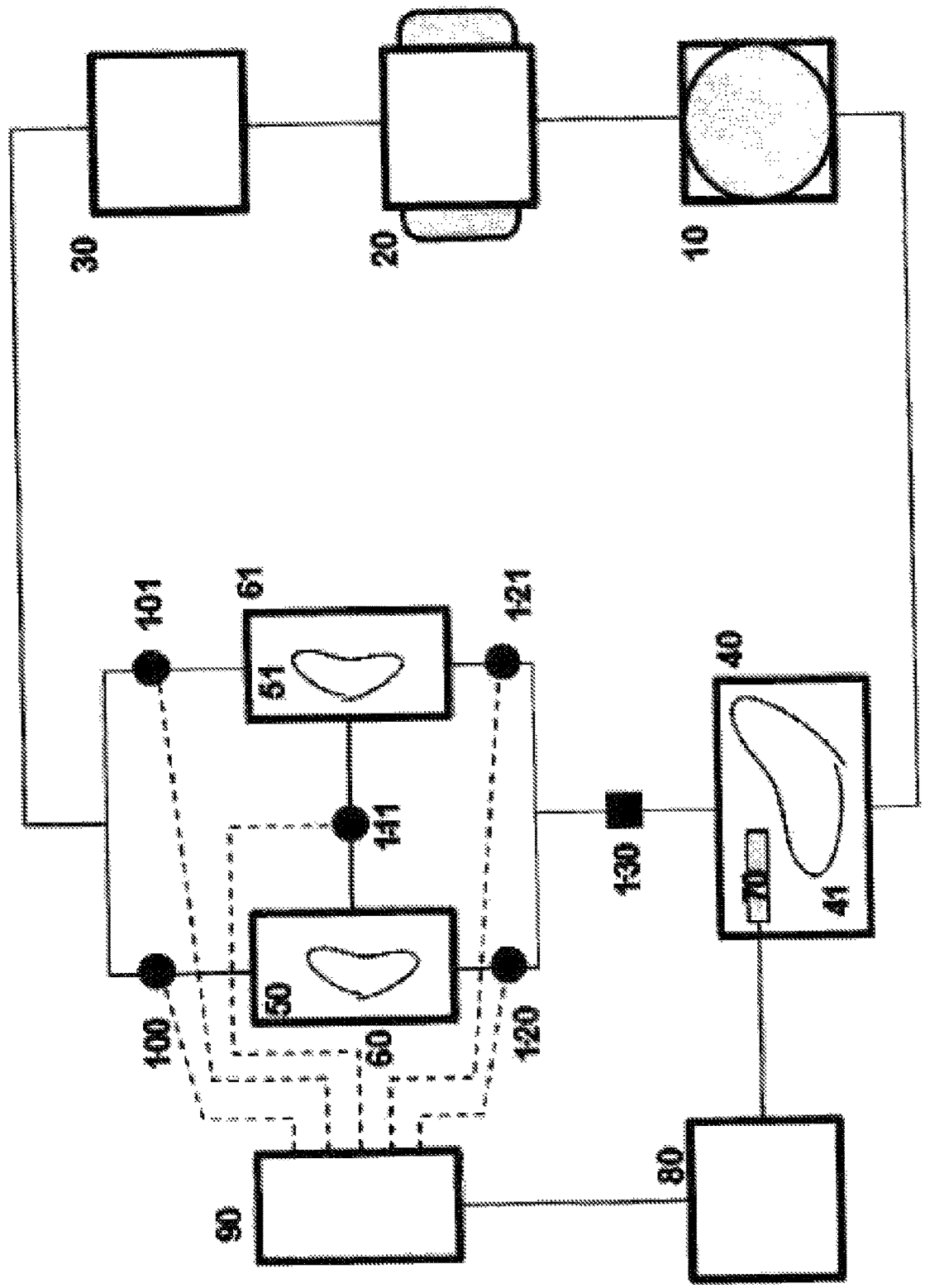
FIG. 22 is a configuration diagram of the illustrative example 8.

A configuration diagram showing the illustrative example 8 of this embodiment is shown in FIG. 22. FIG. 22 is the configuration diagram of the illustrative example 8.

In this illustrative example, a way of preventing the entry of foreign matter such as bubbles, cells, cell debris, and other dirt into the vessel 40 and the pump 10, the gas exchange unit 20, the dialysis unit 30 and the flow paths connecting them is provided.

When foreign matter enters the container 40, it causes clogging or adhesion of the cells or tissue, changing characteristic of or inducing death of the cells or tissue 41 or causing clogging of the flow path(s). When the foreign matter is cells or cell debris, contamination of the cells occurs and normal proliferation and differentiation may be inhibited.

Therefore, in this illustrative example, the container 40 is provided with a mechanism for removing foreign matter 130, such as a column, a filter, a trap, and a branched flow upstream thereof.

The description of the present embodiment including the illustrative examples 1 to 8 is ended here.

OTHER EMBODIMENTS

Although the embodiment of the present invention has been described so far, the present invention may be implemented in various different embodiments within the scope of the technical idea recited in the claims, in addition to the aforementioned embodiment.

For example, the control device for aging induction 100 has been described for the example in which it is configured as a single unit so as to perform processing in a stand-alone form. The present invention, however, is not limited to this and processing may be performed in response to a request from a client terminal such as the external device 200 and the processing result may be returned to the client terminal.

Furthermore, among the processes described in the embodiment, all or some of the processes described as being performed automatically can be performed manually, or all or some of the processes described as being performed manually can be performed automatically by a known method.

Besides, unless otherwise specified, the processing procedures, control procedures, specific names, information including registration data and parameters such as search conditions for each process, screen examples, and database configurations shown in the above documents and drawings can be freely changed.

Regarding the system for aging induction including the control device for aging induction 100 and the culture chambers 40, and the external device 200, each illustrated component is functionally conceptual and is not necessarily required to be physically configured as shown.

For example, all or a part of the processing functions of each device of the control device for aging induction 100, particularly the processing functions performed by the control unit 102, may be realized as a processor such as a central processing unit (CPU) and a program interpreted and executed by the processor, or may be realized as a hardware processor using wired logic. It should be noted that the program is stored in a non-transitory computer-readable recording medium including a programmed command for causing the computer to execute the method according to the present invention, which is described later, and is mechanically read into the control device for aging induction 100 and the external device 200, if necessary. That is, in the memory unit 106 such as a ROM or a hard disk drive (HDD) etc., a computer program for giving commands to the CPU in cooperation with the operating system (OS) and performing processes is stored. This computer program is executed by being loaded into the RAM, and cooperates with the CPU to constitute the control unit.

Moreover, this computer program may be stored in an application program server connected to the control device for aging induction 100 or the external device 200 via any network 300, and all or a part of it can be download, if necessary.

Furthermore, the program according to the present invention may be stored in a computer-readable recording medium, or may be configured as a program product. As used herein, the term "recording medium" includes any "physical medium for portable use" such as a memory card, a USB memory, an SD card, a flexible disk, a magneto-optical disk, a ROM, an EPROM, an EEPROM, a CD-ROM, an MO, a DVD, and a Blu-ray (registered trademark) disc.

In addition, the "program" is a data processing method described using any language or description method, and its format such as a source code, binary code, etc. does not matter. It should be noted that the "program" is not necessarily limited to a single program and include those configured in a distributed manner as a plurality of modules or libraries and those that achieves their function in cooperation with a separate program represented by an operating system (OS). It should be noted that well-known configurations and procedures can be used for specific configurations for reading the recording medium, reading procedures, and installation procedures after reading, in each device described in the embodiments. The present invention may be configured as a program product in which the program is stored in a non-transitory computer-readable recording medium.

Various databases and the like (the file for aging induction 106a, the file for culture chamber arrangement 106b, etc.) stored in the memory unit 106 are storage means such as a memory device such as a RAM and a ROM, a fixed disk device such as a hard disk, a flexible disk, and an optical disk, and store various programs, tables, databases, files for web pages, and the like used for various processing and a website providing.

Furthermore, the control device for aging induction 100 and the external device 200 may be configured as an information processing device such as a known personal computer and a workstation, and any peripheral device may be connected to the information processing device. Moreover, the control device for aging induction 100 and the external device 200 may be realized by implementing software (including programs, data, etc.) for causing the information processing device to realize the method of the present invention.

Further, specific forms of the distribution and integration of the devices are not limited to those shown, and all or a part thereof may be configured by functionally or physically distributing or integrating any number of units according to a variety of additions or according to functional loads. That is, the aforementioned embodiments may be freely combined for implementation or the embodiment may be selectively performed for practice.

DESCRIPTIONS AND COMPARISONS OF RELATED ART

As an additional description on the related art, configurations and operations of the related art are described. JP-A-2001-120261 provides a way for controlling hematopoiesis by differentiating hematopoietic progenitor cells. Specifically, human stem cells are cultured in flow circulation, and a culture medium containing hematopoietic growth factors is flown from a circulation culture system for human hematopoietic progenitor cells placed beside to a circulation culture system for human stem cells. As a result, hematopoiesis from human stem cells is promoted.

In JP-T-2013-510590, provided are articles and methods for growing or analyzing tissues and internal organs, using bioreactors or other devices and components, are provided. In JP-T-2013-510590, cytokine-secreting cells (such as human hematopoietic progenitor cells in JP-A-2001-120261) and the tissue as the subject of which growth is to be induced, such as human stem cells are placed in the same circulation culture system, and the secreted cytokines are carried by the culture medium and reach the tissue as the subject of aging-induction, which results in the growth and differentiation of the tissue as the subject of aging-induction.

JP-T-2008-513013 discloses a method that involves co-culturing different kinds of cells that secrete cytokines, and appropriately changing flow paths to cause a freely-selected specific kind of cytokines for growth and differentiation to act on the cells and tissue to be observed.

Comparison Between Related Arts and this Embodiment

In contrast to JP-A-2001-120261, in the present embodiment, the cytokine-secreting cells and the tissue as the subject of aging-induction are placed in series on the same circulation culture style, and the mechanism of aging and differentiation and a control method are different.

In contrast to JP-T-2013-510590, in the present embodiment, different kinds of cytokine-secreting cells can act on the tissue as the subject of aging-induction, so that more complicated cytokine control is achieved.

In contrast to JP-T-2008-513013, the present embodiment is configured such that not only a plurality of cytokine-secreting cells can act on the tissue as the subject of aging-induction but also cytokine-secreting cells can interact with each other, which achieves a more complex cytokine metabolism. As a result, more sophisticated cytokine control can be performed on the tissue as the subject of aging-induction.

Different cytokines are required at different stages in cell proliferation, differentiation, or development of tissues and internal organs. The present embodiment provides means for obtaining different cytokines depending on the stages. More specifically, a plurality of types of cytokine-secreting cells A and B is placed in series on flow paths of which order can be changed and are cultured in circulation. Here, the cytokine-secreting cells B placed downstream can be converted to secrete another kind of cytokines C in place of B that they usually secrete, in response to cytokines A secreted by the cytokine-secreting cells A placed upstream.

Control of cytokine secretion can result in the control the proliferation and differentiation of undifferentiated cells, aging and differentiation of immature tissues and internal organs. As applied way of use, it is possible to observe long-term preservation of internal organs and reactions of internal organs to external factors. The conversion of cytokine-secreting cells is controlled by changing the flow paths for the culture medium automatically using a variety of sensors or manually.

REFERENCES

1. Japanese Patent No. 5881422, "Methods and devices for perfusion culture of internal organs or tissues"
2. JP-A-2001-120261, "Methods for culturing and transforming human stem cell-containing compositions"
3. JP-T-2013-510590, "Bioreactors, systems, and methods for producing and/or analyzing organs"
4. JP-T-2008-513013, "Perfusion bioreactors for culturing cells"
5. Japanese Patent No. 5797113, "Methods of producing bioartificial organs"

(Note 1)
A device for aging induction including:
first means for spreading, when the subject of aging-induction is a cell or tissue, a culture medium over a culture layer and culturing the subject of aging-induction over a prolonged time period, or filling, when the subject of aging-induction is an internal organ, a blood vessel in the cultured internal organ with a culture medium and culturing the subject of aging-induction over a prolonged time period:
second means for spreading a culture medium over a cell type that secretes a cytokine and culturing the cultured internal organ over a prolonged time period:
third means for causing a cell type that secretes a cytokine to secrete a cytokine;
fourth means for spreading a culture medium containing a cytokine over the culture layer or the cultured internal organ as the subject of aging-induction; and fifth means for controlling a flow rate of a culture medium containing the cytokines.
(Note 2)
A device for inducing aging of a cell or tissue or internal organ, the device including:
a first kind of cytokine-secreting cell or tissue (50);

a cytokine-secreting tissue container (60) for storing the cytokine-secreting cell or tissue (50):
  a second kind of cytokine-secreting cell or tissue (51);
  a cytokine-secreting cell or tissue container (61) for storing the cytokine-secreting organ secreting cell or issue (61);
  a valve (1-00) for controlling the amount of inflow of a culture medium into the container (60):
  a valve (1-01) for controlling the amount of inflow of the culture medium into the container (61);
  a valve (1-11) for controlling the flow rate of the culture medium between the containers (60) and (61);
  a valve (1-20) for controlling the amount of outflow of the culture medium from the container (60);
  a valve (1-21) for controlling the amount of outflow of the culture medium from the container (61), downstream thereof, a cell or tissue or internal organ (41);
  a vessel (40) for storing the cell or tissue or internal organ (41):
  a sensor unit (70) for detecting the state of the cell or tissue or internal organ 41;
  an input unit (80) for receiving an external input such as a signal from the sensor (70); and
  a valve opening/closing control unit (90) for controlling the opening and closing of the valves (1-00, 1-01, 1-11, 1-20, and 1-21) based on the signal from the input unit (80).

(Note 3)
The device for aging induction described in Note 2, further including:
  a third kind of cytokine-secreting cell or tissue (52);
  a cytokine-secreting cell or tissue container (62) for storing the cytokine-secreting cell or tissue (52);
  a valve (1-02) for controlling the amount of inflow of the culture medium into the container (62);
  a valve (1-10) for controlling the flow rate of the culture medium between the containers (60) and (62):
  a valve (1-12) for controlling the flow rate of the culture medium between the containers (61) and (62); and
  a valve (1-22) for controlling the amount of outflow of the culture medium from the container (62).

(Note 4)
The device for aging induction described in Note 2 or 3, wherein
the container (60) for the cytokine-secreting cell or tissue (50) includes a flow circulation system consisting of a pump (611), a gas exchange unit (612), and a dialysis unit (613).

(Note 5)
The device for aging induction described in any one of Notes 2 to 4, further including:
  at a position of the valve (1-00, 1-01, 1-02, 1-10, 1-11, 1-12, 1-20, 1-21, 1-22) on the flow path, a mechanism for removing foreign matter such as air bubbles, cells or cell debris, and other dirt from the flow path system, such as a column, a filter, and a flow path branch provided with a valve.

(Note 6)
The device for aging induction described in any one of Notes 2 to 5, further including:
  at any or all position(s) of the valve(s) (1-00, 1-01, 1-02, 1-10, 1-11, 1-12, 1-20, 1-21, 1-22) on the flow path, a mechanism for eliminating physiological activity of a certain organic compound, inorganic compound, protein and the like by a method such as decomposition, removal, inactivation, etc. thereof by heating, filtration, adsorption, selective chemical reaction, etc.

(Note 7)
The device for aging induction described in any one of Notes 2 to 6, further including:
  a gas exchange unit (20) for supplying oxygen to the culture medium and eliminating carbon dioxide; and
  a dialysis unit (30) for removing waste matter from the culture medium, wherein
  the culture medium is circulated and reused.

(Note 8)
The device for aging induction described in any one of Notes 2 to 7, wherein the vessel (41) for storing the cell or tissue or internal organ (40) includes a filter or removing device (130) that does not pass cells or cell debris or other dirt through.

(Note 9)
A method for aging induction including steps for achieving functions of the device for aging induction described in any one of Notes 2 to 8.

(Note 10)
A method for aging induction including:
  a first step for spreading, when the subject of aging-induction is a cell or tissue, a culture medium over a culture layer and culturing a subject of aging-induction over prolonged time periods, or filling, when the subject of aging-induction is an internal organ, a blood vessel in a cultured internal organ with a culture medium and culturing a subject of aging-induction over prolonged time periods;
  a second step for spreading a culture medium over a cell type that secretes a cytokine and culturing the cultured internal organ over prolonged time periods;
  a third step for causing a cell type that secretes a cytokine to secrete a cytokine;
  a fourth step for spreading a culture medium containing a cytokine over the culture layer or the cultured internal organ as the subject of aging-induction; and
  a fifth step for controlling a flow rate of a culture medium containing a cytokine.

(Note 11)
A program for aging induction for causing a computer to execute a method including:
  a first step for spreading, when the subject of aging-induction is a cell or tissue, a culture medium over a culture layer and culturing the subject of aging-induction over prolonged time periods, or filling, when the subject of aging-induction is an internal organ, a blood vessel in the cultured internal organ with a culture medium and culturing the subject of aging-induction over prolonged time periods;
  a second step for spreading a culture medium over a cell type that secretes a cytokine and culturing the cultured internal organ over prolonged time periods;
  a third step for causing a cell type that secretes a cytokine to secrete a cytokine;
  a fourth step for spreading the culture medium containing a cytokine over the culture layer or the cultured internal organ as the subject of aging-induction; and
  a fifth step for controlling a flow rate of the culture medium containing a cytokine.

INDUSTRIAL APPLICABILITY

As described above in detail, according to the present invention, it is possible to provide devices for aging induction, methods for aging induction, and programs for aging induction with which culture can be performed without the need to add growth factors at different stages of aging of internal organs.

DENOTATION OF SYMBOLS 1 valve
10 pump
20 gas exchange unit
30 dialysis unit
40 culture chamber (vessel)
41 cell tissue
50, 51 secretory tissues
60, 61, 62 secretory tissue container
70 sensor
80 inputting device
90 control unit
100 control device for aging induction
102 control unit
102a aging state detection unit
102b flow rate control unit
104 communication control interface unit
106 memory unit
106a file for aging induction
106b file for culture chamber arrangement
108 input/output control interface
112 input unit
114 output unit
130 mechanism for removing foreign matter
200 external device
300 network
601 pump
602 gas exchange unit
603 dialysis unit
901 culture procedure data
902 culture procedure database
903 position information
904 valve opening/closing procedure generating unit
905 valve opening/closing control unit

The invention claimed is:

1. A system for aging induction comprising:
a $1^{st}$ culture chamber for perfusing, with a culture medium, a subject of aging-induction, the subject of aging-induction being derived from a living organism;
a set of $2^{nd}$-$n^{th}$ culture chambers, each chamber of the set being for perfusing a secretor with a culture medium, the secretor secreting a cytokine, the set of $2^{nd}$-$n^{th}$ culture chambers being arranged in series in fluid connection with each other; and
a control device for aging induction comprising:
 a detection unit;
 a memory unit; and
 a control unit comprising:
  an aging state detector for detecting, via the detection unit, an aging state of a subject of aging-induction; and
  a flow rate controller for controlling a flow rate at which the culture medium containing the cytokine secreted by the secretor is supplied to the subject of aging-induction, according to the aging state of the subject of aging-induction, wherein:
the $1^{st}$ culture chamber is connected to the $2^{nd}$ culture chamber in fluid connection;
the $1^{st}$ culture chamber and the $n^{th}$ culture chamber are further in fluid connection with each other such that the culture medium with which the subject of aging-induction has been perfused in the $1^{st}$ culture chamber is circulated to the $n^{th}$ culture chamber;
the subject of aging-induction is a cell, a tissue or an organ;
the secretor is a cell, a tissue or an organ; and
the aging state of the subject of aging-induction comprises a differentiation stage, growth stage and development stage.

2. The system for aging induction according to claim 1, wherein
a tube is provided between the culture chambers;
the flow rate is controlled via a valve provided in the tube.

3. The system for aging induction according to claim 1, wherein
the flow rate is controlled via a robot that moves liquid between the culture chambers.

4. The system for aging induction according to claim 1, wherein
the cytokine is selected from a group consisting of a hormone, lymphokine, chemokine, monokine, myocaine, interleukin, interferon, hematopoietic factor, cell growth factor, tumor necrosis factor (TNF), adipokine, neurotrophic factor, antibody, humoral ligand, neurotransmitter, signaling molecule, and chemotactic attractant.

5. The system for aging induction according to claim 1, wherein a unit comprising a new culture medium is arranged between two culture chambers in the series of the culture chambers.

6. The system for aging induction according to claim 5, wherein the unit comprising a new culture medium is placed between the $1^{st}$ culture chamber and the $n^{th}$ culture chamber.

7. The system for aging induction according to claim 1, wherein the system comprises a $1^{st}$, a $2^{nd}$, and a $3^{rd}$ culture chamber.

8. The system for aging induction according to claim 1, wherein the system comprises a $1^{st}$, a $2^{nd}$, a $3^{rd}$, and a $4^{th}$ culture chamber.

* * * * *